US006635248B1

(12) United States Patent
Ternynck et al.

(10) Patent No.: US 6,635,248 B1
(45) Date of Patent: Oct. 21, 2003

(54) SINGLE-CHAIN ANTIBODY FRAGMENTS FOR TRANSFERRING SUBSTANCES INTO CELLS

(75) Inventors: Therese Ternynck, Paris (FR); Alexandre Avrameas, Vitry sur Seine (FR); Gerard Buttin, Paris (FR); Stratis Avrameas, Paris (FR); Marie-Francoise Saron, Paris (FR); Bruno Blondel, Bures sur Yvette (FR); Therese Couderc, Paris (FR); Susan Michelson, Noisy (FR); Donato Zipeto, Paris (FR)

(73) Assignees: Institut Pasteur, Paris (FR); Universite Pierre et Marie Curie, Paris (FR)

( * ) Notice: Subject to any disclaimer, the term of this patent is extended or adjusted under 35 U.S.C. 154(b) by 0 days.

(21) Appl. No.: 09/497,997

(22) Filed: Feb. 4, 2000

Related U.S. Application Data

(63) Continuation of application No. PCT/FR98/01740, filed on Aug. 4, 1998.

(30) Foreign Application Priority Data

Aug. 4, 1997 (FR) ............................................. 97 09972

(51) Int. Cl.⁷ ........................ A61K 39/395; C07K 1/00
(52) U.S. Cl. ................ 424/135.1; 424/130.1; 424/133.1; 424/134.1; 424/178.1; 530/300; 530/350; 530/387.1
(58) Field of Search ............ 424/130.1, 133.1, 424/134.1, 178.1, 135.1; 530/300, 350, 387.1; 514/44; 435/4

(56) References Cited

U.S. PATENT DOCUMENTS

| 5,296,348 A | | 3/1994 | Rakowicz-Szulczynska et al. ................................. 435/6 |
| 5,521,291 A | | 5/1996 | Curiel et al. .............. 530/391.7 |
| 5,597,573 A | * | 1/1997 | Kamireddy et al. ...... 424/234.1 |
| 5,606,017 A | | 2/1997 | Willner et al. ............... 530/322 |
| 5,635,383 A | | 6/1997 | Wu et al. ................. 435/172.3 |
| 5,733,782 A | | 3/1998 | Dorai et al. ................. 435/328 |
| 5,861,156 A | * | 1/1999 | George et al. ........... 424/135.1 |

OTHER PUBLICATIONS

Jin et al, The anticoagulant activation of antithrombin by heparin, PNAS USA 94:14683–14688 (Dec. 1997).*

Zack et al, "DNA Mimics a Self–Protein that may be a Target for some Anti–DNA Antibodies in Systemic Lupus Erythematosus", Journal of Immunology, vol. 154, 1995, pp. 1987–1994, XP002063314.

Zack et al, "Mechanisms of Cellular Penetration and Nuclear Localization of an Anti–Double Strand DNA Autoantibody", Journal of Immunology, vol. 157, 1996, pp. 2082–2088.

Vlahakos et al, "Murine Monoclonal Anti–DNA Antibodies Penetrate Cells, Bind to Nuclei and Induce Glomeular Proliferation and Proteinuria in vivo", Journal of the American Society of Nephrology, vol. 2, 1992, pp. 1345–1354, XP002063435.

Avrameas: Polyreactive Anti–DNA Monoclonal Antibodies and a Derived Peptide as Vectors for the Intracytoplasmic and Intranuclear Translocation of Macromolecules: PNAS, vol. 95, May 1998, pp. 5601–5606, XP002087950.

* cited by examiner

*Primary Examiner*—Hankyel T. Park
*Assistant Examiner*—Stacy S. Brown
(74) *Attorney, Agent, or Firm*—Oblon, Spivak, McClelland, Maier & Neustadt, P.C.

(57) ABSTRACT

The present invention provides novel polypeptides which can effectively penetrate into cells thereby transporting a substance of interest into the cells.

21 Claims, 13 Drawing Sheets

```
             10        20        30         40              50 52A    60
                                 CDR1                        CDR2
        GGSLKLSCAASGFTFSSYAMSWVRQTPAKRLEWVAYISRGGGIFYYQDSIKGRFTI
J20.8   
F4.1    ET----------------------------------------VST--S-TV---
F14.6   ALVKP---------------N-G-----------E-------------A------------YS--L--V---
H9.3    ELVR-A-V-V-CTT----NIKDDYIH------R-EQG----IGR-DPAN-KTK-APKFQDKA---
A2.1    GLVKP-A-V-V---NV--YS--TG-F-N---------SHG-S--------GR-NPLN-DIF-NQKF--KA-L 70      80 ABC   90
                            CDR3
        ARDNAKNTLYLQMSSLRSEDTAMYYCTREKY..GKRG.MDYWGQGTSVTVSS
J20.8   
F4.1    S-------S---------------------Q--N.--A.--------------
F14.6   S------R---------E--------A-TAR..ATWDWFA------L----A
H9.3    TA-TSS--A--L--T----V--S-SNYYGNSPSWFA------------A
A2.1    TV-KSS--AHMELR--K--NS-V-CA-GL...T-WYF-V--A--T--L-A

FIG.2

CDR2                         CDR3
        YISRGGGIFYYQDSIKG            EKYGKRG   MDY  (J20.8)
        ----VST--S-TV---             QKYNKRA   MDY  (F4.1)
        A-----YS--L--V---            TARATWDW  FAY  (F14.6)

FIG.3
```

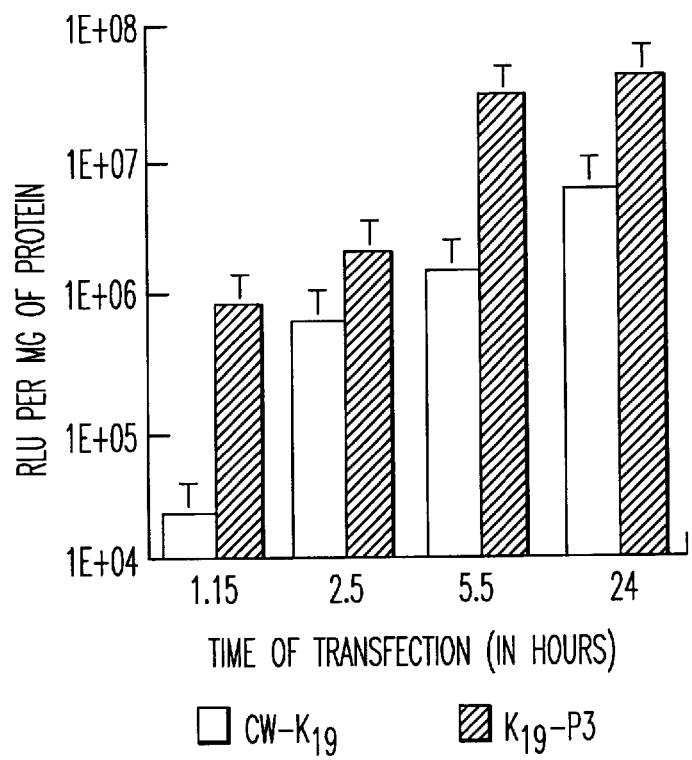
FIG. 7
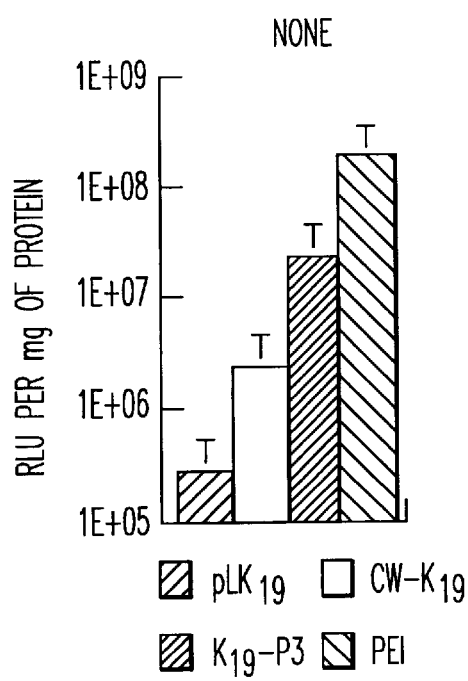 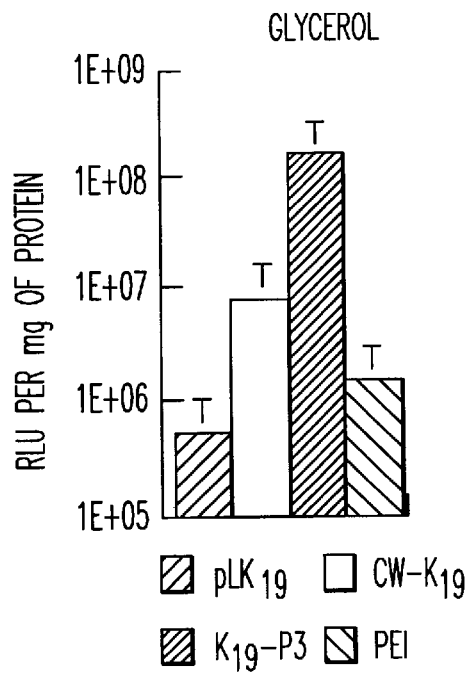
FIG. 8A    FIG. 8B

SINGLE-CHAIN ANTIBODY FRAGMENTS FOR TRANSFERRING SUBSTANCES INTO CELLS

CROSS-REFERENCE TO A RELATED APPLICATION

The present application is a continuation of PCT/FR98/01740 filed Aug. 4, 1998.

BACKGROUND OF THE INVENTION

1. Field of the Invention

The present invention relates to active transfer of haptens, proteins, peptides, nucleic acids and other molecules into cells. More particularly, the present invention relates to novel polypeptides which can effectively penetrate into cells, in particular eukaryotic cells, and transport thereto a substance of interest which is capable of constituting novel antiviral compositions. This invention is of major importance as it has application in a variety of fields, in particular that of gene therapy and vaccines.

2. Description of the Background

Gene therapy remains dependent on a considerable number of parameters, among them the development of vectors which are capable of transferring active principles endowed with predetermined specific properties to the cytoplasm of cells of the host organism under consideration in the absence of genetic alterations associated with the use of such vectors, and with no degradation of the biological activity of the transferred active principles. Current knowledge is that in spite of the effort achieved in developing vectors of viral or non viral origins, not all of these conditions have been satisfactorily fulfilled.

Further, the possibility of transporting substances efficiently into cells is also important for all biotechnological applications. Thus transferring substances into cells in vitro or ex vivo can be used either to produce proteins or peptides, or to regulate gene expression, or to analyse the properties of a given substance in that cell. In vivo, the transfer of a substance to a cell can also act to create models for studying diseases in animals or for studying the effect of a given compound on an organism.

The present invention thus aims to provide a novel type of vector which is both effective and is more innocuous than viral vectors in current use.

International patent application WO 97/02840 describes the use of antibodies or their F(ab')2 and Fab' fragments which can penetrate into the interior of living cells, as immunovectors for intracytoplasmic and intranuclear transfer of biologically active substances. While such vectors are highly effective, their use can produce problems in some applications. The use of antibodies or F(ab')2 antibody fragments involves the production of high titers of these molecules with qualities which are compatible with therapeutic use. Further, the use of molecules with the size and complexity of antibodies can constitute a further disadvantage, in particular as regards use. U.S. Pat. No. 5,635,383 illustrates a further type of complex vector based on polylysine for transferring nucleic acids into cells.

The present application relates to novel polypeptides with advantageous properties both for transferring of substances into cells and as antiviral agents. The primary structure of these polypeptides is much simpler than antibodies and they are of reduced size. Further, preparation is easy and their potential applications are highly varied.

More particularly, the present invention stems from the discovery by the inventors that it is possible to identify, from whole antibodies, limited regions carrying a cellular penetration activity. The invention also stems from the discovery that it is possible to isolate, from whole antibodies, in particular from a single chain of these antibodies, peptides or polypeptides endowed with cell penetration activity. The present invention constitutes the first demonstration that a fragment of a single chain of an antibody can effectively penetrate into cells. The present invention also constitutes the first demonstration that such a fragment is also capable, advantageously, of transporting a substance of interest into said cell, and can preferably have an antiviral activity.

SUMMARY OF THE INVENTION

The present invention thus provides novel molecules which are particularly adapted to transfer biologically active substances into eukaryotic cells, particularly mammalian cells.

In a first aspect, the invention provides a polypeptide characterized in that:
  it is constituted by a unique or repeated peptide motif; and
  it comprises an amino acid sequence endowing it with the capacity to penetrate into cells and, if necessary, to transport thereto a substance of interest.

In this regard, the invention concerns a polypeptide characterized in that:
  it is constituted by a unique or repeated peptide motif; and
  it comprises an amino acid sequence constitute by one or more different antibody fragment(s); and
  it is capable of penetrating into cells.

In one implementation of the invention, the polypeptides thus comprise one or more fragment(s) of an antibody which may or may not be different. In their simplest form, antibodies (molecules from the immunoglobulin superfamily) are constituted by four chains which are associated together (for example IgG) two heavy chains H, and two light chains L (FIG. 1). These four chains are associated together post-synthesis to form a molecule with a molecular weight of about 150,000 kD. The antigenic specificity of antibodies is provided by variable domains involving a number of regions of a heavy chain and a number of regions of a light chain (FIG. 1).

Polypeptides can also be constituted by sequences originating from other immunoglobulin representatives such as IgM.

Each heavy chain of an antibody is composed of about 450 amino acids, and comprises different domains termed the constant domain (C), variable domain (V) and joining domains (D and J). Particular motifs are found in the variable domains, termed CDR (Complementarity Determining Region) which can readily be localised by sequence alignment (C. Janeway and P. Travers, 1996, Immunobiology, Academic Press, "The Structure of a Typical Antibody Molecule"). For an analysis of the sequences of the variable regions, reference should also be made to the article by T. T. Wu and E. Kabat (J. Exp. Med., 1970, Vol. 132, p. 211–250). CDR motifs themselves comprise hypervariable regions.

The present application stems from the demonstration that it is possible to obtain regions which are limited in size and of simple structure with particularly advantageous properties from the antibody structure. Thus, starting from a molecule which is complex (four associated chains) and large (150000 kD), the Applicant has succeeded in constructing polypeptides with a single chain, with the capability of penetrating into cells and of transporting thereto substances of interest. The properties of the polypeptides of the invention are all the more remarkable since their sequences corresponding to those of one or more fragments of only one of the chains of an antibody and thus in order to be active, there is no need for constant regions originating from a heavy chain and a light chain. Polypeptides of the invention obtained by chemical synthesis have the same properties.

The term "polypeptide" as used in the present invention defines a molecule comprising a concatenation of amino acids, with a size in the range 3 to 100 amino acids, for example less than 60 amino acids. Still more preferably, it is a molecule comprising a concatenation of 3 to 60 amino acids, advantageously 3 to 30. Particularly preferred polypeptides advantageously comprise more than about 10 amino acids. The polypeptide of the invention can also comprise certain structural modifications, of a chemical or enzymatic nature for example. Thus the polypeptide of the invention can comprise certain functional groups which, by chemical or enzymatic reaction, can couple with another substance. The polypeptides of the invention can also be chemically modified in order to render them more resistant to proteases or less visible to the immune system. The polypeptides of the invention can be obtained by any method which is known to the skilled person, in particular by chemical synthesis, for example using peptide synthesisers, or by fragmentation or deletion from larger polypeptides, natural or otherwise. They can also be prepared using recombinant DNA techniques, by expression of a corresponding nucleic acid in a eukaryotic or prokaryotic host cell. Clearly, they can result from combinations of these different methods.

To this end, the polypeptides of the invention can be produced from libraries of nucleic acids or peptides, such as synthesised combinatorial libraries.

The term "unique peptide motif" means that, in contrast to antibodies or Fab or F(ab')2 type antibody fragments, for example, the polypeptides of the invention comprise only a single chain of amino acids. The term "repeated peptide motif" means that the polypeptides of the invention can comprise different peptide blocks assembled together, optionally chemically, to form a single chain.

The term "penetrate" or "penetrating" as used in the present invention means a polypeptide which is capable of passing from the external medium to the intracellular medium, in particular into the cell cytoplasm. This capacity can be determined in different manners, in particular using a cell penetration test comprising initial incubation of the polypeptide to be studied in the presence of culture cells followed, after fixing and permeabilisation of these cells, by revealing the presence of said polypeptide inside said cell. Revealing can be achieved by a further incubation with labelled antibodies directed against said polypeptide and detection, in the cytoplasm or in the immediate proximity of the nucleus or even in the nucleus, of the antigen-antibody type immunological reaction between the polypeptlde and the labelled antibody. A previously labelled polypeptide of the invention followed by detection of said labelling in these cellular compartments can also be used for revealing. Such a cell penetration test has been described, for example, in International patent application WO 97/02840.

As indicated above, the present invention stems from demonstrating the existence of reduced regions of an antibody endowed with cell penetration properties and which can also act to transport substances of interest. More particularly, the inventors have sought the presence of regions endowed with cell penetration properties and which could be used as a vector in place of whole antibodies in the structure of certain penetrating antibodies such as those described in WO 97/02840. To this end, the inventors have first determined the complete sequence of heavy and light chains of three particular monoclonal antibodies, J20.8, F4.1 and F14.6. These antibodies are anti-DNA antibodies, polyreactive, which are produced by hybridoma deposited at the CNCM [National Collection of Micro-organism Cultures] under numbers I-1605, I-6506 and I-1607 (see patent application cited above). Alignment of these sequences and their comparative analysis have revealed the following remarkable elements:

the existence of a region of very high homology (65–70%) in the CDR2 region of these three antibodies; and the presence, in these three antibodies, of CDR3 regions which are rich in lysine and arginine (basic amino acids).

With regard to these results, and given that the majority of peptides capable of transport and nuclear localisation are rich in lysine and arginine, the Applicants then synthesised series of polypeptides corresponding to different regions of these antibodies, and in particular to the CDR2 and CDR3 regions, and hybrid constructions in which certain of these regions were fused together (in particular a CDR2–3 peptide carrying CDR2 and CDR3 regions in succession). A biotin residue was also introduced to the N-terminal side of these polypeptides, to enable them to be detected easily.

These polypeptides were then tested for their capacity to penetrate into cells. The results obtained show that, remarkably, certain of these polypeptides have the capacity to penetrate effectively into cells. In particular, the results obtained show that the group of polypeptides which comprise all or a portion of the CDR3 region are capable of penetrating into cells.

More preferably, the polypeptides of the invention are thus constituted by a unique chain comprising at least one fragment of the heavy chain of an antibody. Still more preferably, they comprise at least a fragment of the variable region of the heavy chain of an antibody.

In a particular implementation, the invention concerns polypeptides as defined above comprising all or a portion of the CDR3 region of an antibody.

Further, the results obtained have also shown that polypeptides also containing all or a portion of the CDR2 region also have the capability of penetrating into cells. To this end, polypeptides which combine all or a portion of the CDR3 region and all or a portion of the CDR2 region have entirely remarkable cell penetration capacities.

Thus in a further implementation, the polypeptides of the invention comprise all or a portion of the CDR2 region of an antibody.

In a particularly interesting implementation, the polypeptides of the invention more preferably comprise all or a portion of the CDR3 region and all or a portion of the CDR2 region. This type of polypeptide is particularly advantageous as it is capable of mass penetration into the interior of living cells.

More particularly, the expression "all or a portion" as used in the present application means that the polypeptides of the invention can comprise either the whole of the CDR region concerned of an antibody, or only a portion thereof, it being understood that the polypeptide retains a cell penetration capacity (functional homologue). A portion of the CDR region can consist of a CDR region which is free of one or more terminal amino acids, in particular one, two or three terminal amino acids. It may also be a CDR region where one or more internal residues have been deleted or substituted by other amino acids, preferably amino acids of the same nature (for example basic amino acids). Advantageously, less than 30% of the internal residues of the CDR region are modified, preferably less than 20% and more preferably less than 15%.

Preferred polypeptides of the invention are thus polypeptides comprising all or a portion of a CDR3 region of an antibody. By way of illustration, CDR3 regions with sequence SEQ ID NO 1, 2, 3, 8 or the sequences shown in FIG. 2 and FIG. 3 or any functional homologue can be cited.

The antibody fragments can themselves constitute the polypeptide of the invention. They can also be modified by adding residues to one or both of their extremities. In particular, it may be advantageous to add amino acids which give the fragment, in particular the CDR region, a better spatial configuration. It may also be advantageous to add one or more essentially basic amino acids, lysine and/or arginine in type, to stabilise the polypeptide and increase its interaction with the cell membranes. Further, as indicated above, the polypeptides of the invention may comprise several regions of an antibody chain, such as a CDR2 region and a CDR3 region. These regions can in particular be fused together or spaced by amino acids as described above.

Particular polypeptides of the invention are polypeptides comprising a CDR3 region of an antibody or polypeptides essentially comprising a fusion between the CDR3 region of an antibody and the CDR2 region of an antibody. Examples of such polypeptides are the CDR3 polypeptides and the CDR2–3 polypeptide the sequences for which are given in the Examples.

Experiments carried out with these polypeptides, in particular polypeptides comprising the CDR3 region, and more particularly those comprising the CDR3 region and the CDR2 region, clearly show that:

1) incubating PtK2, HeLa or 3T3 cells for one hour with complete culture medium (10% foetal calf serum) containing the polypeptide is sufficient for the polypeptide to be massively transported into the cytoplasm of all the cells and into the nucleus of a large proportion of these cells, the proportion being variable depending on the line concerned.

2) When cells are incubated for 2 hours in complete culture medium containing pre-formed peptide-streptavidin complexes coupled to peroxidase (MW≧100000) or peptide-streptavidin coupled to alkaline phosphatase (MW≧180000), the corresponding enzymes are detected in the cytoplasm of all of the cells of the culture and weakly to intensely detected in the majority of the nuclei of these cells. No intracellular coloration is observed when the cells are incubated in the presence of streptavidin coupled with peroxidase, streptavidin coupled with alkaline phosphatase or with streptavidin or the enzymes in their native forms.

The polypeptides of the invention, in particular of type CDR3 and CDR2–3, and their peptide-streptavidin-enzyme complexes are transported in large quantities into a large proportion of human peripheral cells and particularly into activated T lymphocytes.

In general, the polypeptides of the invention can be constructed using different techniques which are known to the skilled person (supra), starting from any given antibody, in particular any given monoclonal antibody.

Preferably, the polypeptides of the invention are obtained by chemical synthesis or are constructed from a fragment or several fragments of one or more penetrating antibody(ies), preferably a penetrating monoclonal antibody. The existence of antibodies which can penetrate inside cells and in particular into the nuclei of human lymphocytes when these cells are incubated in vitro in a culture medium containing a serum originating from patients with disseminated lupus erythematosus (DLE) was reported for the first time by Alarcon-Segovia et al. In 1978 (Nature, 271). Recently, this type of antibody has been detected in the lupus mouse MRL lpr/lpr, but also in the NZB mouse with an autoimmune hemolytic disease syndrome and even in the normal BALB/c mouse. Certain monoclonal antibodies prepared from the spleen of these mice have been shown to be capable of penetrating in vitro into the nucleus of cells maintained in culture (Vlahakos et al., J. Am. Soc. Nephrol. 2 (1992) 1345; Eyal Raz et al., Eur. J. Immuno. 23 (1993) 383). Further, it has been shown that these antibodies are also capable, when injected into mice, of penetrating into several types of cells, and are found in their nuclei (Okudaira et al., Arthritis and Rheumatism, 30 (1987) 669).

In general, any antibody can be selected with a view of determining its penetrating character. This selection can be made, for example, using a cell penetration test comprising initial incubation of the antibody under study in the presence of cells, in particular cells into which it is desired to transport a substance of interest, followed by fixing and permeabilisation of these cells, revealing the presence or the absence of this antibody in the plasmic membrane, the cytoplasm or in the immediate proximity of the nucleus or even in the nucleus. Revealing can, for example, be effected by incubation with a second labelled antibody, directed against the test antibody, followed by detection of the immunological reaction of the antigen-antibody type between these two antibodies. Such a test has been described in detail, for example in French patent FR-9508316.

Still more preferably, the fragment of antibody used to construct a polypeptide of the invention is a fragment of a polyreactive antibody, in particular penetrating and polyreactive. A polyreactive antibody is an antibody which is capable of recognising several different antigens. In general, such antibodies have a particularly high affinity for a particular type of antigen and are capable of recognising one or more other antigens with a lower affinity. The polyreactivity of antibodies can be demonstrated by any conventional immunological technique, such as the methodology described by Sibille et al. (Eur. J. Immuno. 1997, 27: 1221–1228).

Advantageously, the polyreactive antibodies used in constructing the polypeptides of the invention are capable of reacting with nucleic acids, free or complexed with proteins (anti-DNA antibodies). This property can be demonstrated using the ELISA technique or by passing the antibodies over a column or any other support on which DNA has already been immobilised. The anti-DNA antibodies are thus retained on the support and can be eluted and isolated using conventional techniques. In general, the avidity for DNA of the anti-DNA antibodies used in the context of the invention is of the order of $1\times10^6$ M to $2\times10^7$ M. Preferably, these antibodies recognise genomic DNA, in particular genomic DNA. In a particular implementation, the antibodies used are polyreactive antibodies which recognise the genomic DNA of human hematopoietic cells. Still more preferably, they are antibodies which are capable of reacting with nucleic acids and recognise, inter alia, proteins such as Tat from the HIV retrovirus, and/or constituents of the cell surface and of the cell cytoskeleton.

To construct a polypeptide of the invention, the selected antibody is then used as follows:

a) if the sequence of the variable region of the heavy or light chain of this antibody is not accessible, it is determined in a first stage. Conventional sequencing techniques can be used, as illustrated in the examples;

b) the CDR regions are localised by sequence alignment with other sequences of antibody chains, or by any other technique;

c) fragments of this sequence are prepared, or the polypeptides corresponding to regions of this sequence are synthesised, and assembled if necessary. To this end, any conventional technique which is known to the skilled person can be used (peptide sequencers, using a restriction enzyme, ligases, etc . . . );

d) the fragment obtained may be modified by addition, deletion or substitution of amino acids;

e) the cell penetration capacity of the polypeptide obtained is then tested under the conditions described above, also the capacity of transporting substances such as fluorescein or peroxidase.

Optionally, steps c), d) and e) or d) and e) are repeated so as to improve the penetration efficacy or the general properties of the polypeptides of the invention.

In a supplemental subsequent step f), the polypeptide obtained, with the capacity to penetrate into cells, is then used in a coupling reaction with a given substance to generate a vector as will be defined below.

An alternative to this method lies in the use of one or more libraries of nucleic acids or peptides as the starting material. Thus rather than starting from the sequence for an antibody, it is possible to construct, for example by combinatorial chemistry, libraries of peptides or nucleic acids coding for peptides representing functional homologues of the CDR2 or CDR3 antibody regions.

The peptides or combinations of peptides or nucleic acids of these libraries are then prepared, optionally modified and tested for their activity using steps c) to e) of the above method.

Preferably in step c) of the above method, the prepared fragments comprise all or a portion of the CDR3 region of an antibody.

In step d), modifications can, for example, consist of introducing certain supplemental amino acids, either simply for technical reasons (ease of synthesis, coupling between different regions, etc) or for structural or physicochemical reasons. Concerning amino acids for "filling", amino acids which are relatively neutral on the structural and physicochemical level are advantageously used. Regarding structural reasons, as indicated above, adding residues can improve the conformation of the polypeptide and thus potentialise its activity. As an example, introducing nuclear localisation factor sequences (NLF) can increase the intranuclear transfer potentials. Further, it may also be desirable to increase the basic nature of the polypeptides.

To this end, to improve the compaction properties of the polypeptides of the invention, in particular as regards nucleic acids, polypeptides have been constructed which carry lysine residues on the N-terminal side. Advantageously, the number of lysine residues is less than 30, more preferably between 10 and 20.

The results presented in the examples confirm the penetration properties of these polypeptides, and their capacity for effective transport of substances of interest, in particular nucleic acids.

Whatever the additions made, the polypeptide of the invention as prepared, for example, using the above protocol, preferably comprises at most 100 amino acids. Still more preferably, it comprises 3 to 60 amino acids, preferably 3 to 40 amino acids.

In a further aspect, the invention concerns the use of a polypeptide as defined above to transfer substances into cells, in vitro, ex vivo or in vivo.

In a still further aspect, the invention concerns a vector for transferring a substance into a cell, characterized in that it comprises a polypeptide as defined above to which said substance is coupled.

In one implementation of the invention, the polypeptide comprises a sequence of amino acids endowing it with the ability to penetrate into cells enabling it to transport into said cell substances of biological interest which are associated therewith, for example haptens or macro-molecules of hundreds to thousands of kD, such as drugs, proteins or nucleic acids.

The sequence of amino acids and the substances of therapeutic interest associated with it can, for example, be coupled or bonded via covalent or non covalent bonds.

A polypeptide of the invention is advantageously constituted by peptides or macro-molecules with the capability of penetrating into living cells, and more particularly from peptide derivatives of antibodies or antibody fragments as described in International patent application WO 97/02840 or from other peptides comprising one or more hypervariable antibody portions, or synthetic molecules, not directly related to an antibody type structure, which can be obtained, for example, by screening a peptide library for cell penetration.

A particular polypeptide of the invention is thus composed of a unique or repeated peptide motif, and comprises a sequence of amino acids which endow it with the capacity to penetrate into cells and transport a substance of interest thereto, this sequence being capable of being obtained by screening a peptide library for cell penetration. The conditions for screening such libraries have been described above.

A further particular polypeptide of the invention is composed of a unique or repeated peptide motif and comprises a sequence of amino acids which endow it with the ability to penetrate into cells and transport thereto a substance of interest, this sequence being composed of a peptide comprising one or more hypervariable antibody portions.

The coupled substance can be any product of interest, in particular a biological, pharmaceutical or agro-alimentary product. In particular, it may be a nucleic acid, such as a ribonucleic acid or a deoxyribonucleic acid. This nucleic acid can also be from a variety of origins, in particular human, viral, animal, eukaryotic or prokaryotic, plant, synthetic, etc . . . This nucleic acid can also be a variety of sizes, from a simple oligonucleotide to a genome or a fraction thereof. In particular, it may be a viral genome or a plasmid. The substance can also be a protein, such as an enzyme, hormone, cytokine, apolipoprotein, growth factor, etc . . . A particular type of substance is represented by antigens. As indicated below, the polypeptides of the invention can advantageously act as an adjuvant and stimulate the immune response directed against an antigen.

More generally, the substance can be any active principle of a drug, be it a chemical, biochemical or synthetic product.

To enable its transfer into a cell, said substance is thus coupled to a polypeptide of the invention.

The term "coupled" as used in the invention means any type of interaction enabling a physical association between the substance and the polypeptide. Preferably, however, the interaction is sufficiently stable for the vector not to dissociate before cell penetration. For this reason, the preferred coupling is covalent coupling.

Covalent coupling can be effected by different techniques which are known to the skilled person. In particular, it can be effected using maleimide, succinimide, peptide, disulphide and thioether bonds. Reference should be made in this respect to "Bioconjugate Techniques" by Greg T. HERMANSON (Academic Press, 1996).

A particular method consists, for example, of adding a cystein residue which can be readily used for disulphide, thioether, amine or acid bonds to one extremity of the polypeptide of the invention. A further approach consists of chemically coupling a biotin group, which then enables any substance bonded to streptavidin to be coupled. Coupling can also be effected using p-benzoquinone (FR-7537392 and U.S. Pat. No. 4,925,921, for example).

In general, any chemical, biochemical, enzymatic or genetic coupling method which is known in the literature can be used.

Further, a vector of the invention can comprise a polypeptide as described above to which a number of identical or different substances are coupled.

The examples below clearly demonstrate that the polypeptides of the invention have the ability not only to penetrate into cells, but also to transport substances of interest thereto. The examples demonstrate enzyme type protein transport. It should be understood that enzymes can be substituted by any other molecule of interest such as nucleic acids, peptides or drugs, under the same conditions.

The examples also demonstrate the capacity of the peptides of the invention to transfer nucleic acids into cells. For this particular application, coupling between the peptide and the nucleic acid is generally non-covalent coupling, based on ionic interactions, electrostatic interactions or Van der Waals forces. More particularly, when used to transfer nucleic acids into cells, a peptide of the invention advantageously comprises a region constituted by basic amino acids, for example lysine in type, enabling a complex (polyplex) to be formed with the negatively charged nucleic acids. Thus in one particular implementation, the invention concerns the use of a peptide as defined above, carrying a polylysine region, for transferring nucleic acids (i.e., plasmids, cosmids, linear fragments, genes, antigens, antisense, oligonucleotides, etc) into cells. In one particular aspect, the invention thus provides a peptide comprising a polylysine region and a region derived from a penetrating polyreactive antibody, and capable of penetrating into cells. More particularly, the polylysine region advantageously comprises 5 to 30 lysine residues, preferably 5 to 20, which are advantageously not interrupted by other residues. The region derived from the penetrating antibody can be defined as above. Such a polypeptide advantageously comprises less than 100 residues, as explained above.

Further, the fact that the polypeptides of the invention enable massive transport of proteins into cells has also prompted the Applicant to examine the possibility of using them as an intracellular antigen transport agent, endowing them with an adjuvant effect and leading to an increase in the immune response against these antigens. Thus mice received several injections with the streptavidin-peroxidase conjugate alone or complexed with a polypeptide of the invention. The results obtained show that the use of a polypeptide of the invention can increase by on average 4 to 8 times the titer of anti-streptavidin antibodies and anti-peroxidase antibodies.

The invention also concerns a method for transferring a substance into a cell in vitro, ex vivo or in vivo comprising:
coupling said substance to a polypeptide as defined above; and
bringing the cell into contact with the product of said coupling.

For in vitro or ex vivo use, contact can be effected by simple incubation of the cells with the coupling product (vector). For in vivo use, contact is generally effected by administering the coupling product (vector) to the organism under consideration. As indicated above, when coupling is covalent in type, the vector can comprise one or more molecules of interest. Further, for non-covalent coupling, for example for nucleic acids, the vector is generally formed by incubating the peptide and the nucleic acids in a medium enabling them to form a complex. The respective quantities of the partners are easily adjusted by the skilled person as a function of the nature of the peptide (length and charge), nucleic acid and cell type. By way of example, coupling can be carried out at peptide concentrations of 0.01 to 100 nmoles of peptide per µg of nucleic acid, preferably 0.01 to 10 nmoles/µg. Further, in the method of the invention, it may be advantageous to use, in addition, a stabilising agent or facilitator such as glycerol. Thus the results shown in the examples show that in the presence of glycerol, the transfection efficacy of nucleic acids can be improved by a factor of close to 40. Thus a particular implementation of the method of the invention comprises bringing cells into contact with the coupling product in the presence of a stabilising agent, in particular glycerol. Advantageously, transfection is carried out in vitro or ex vivo in the presence of glycerol, at concentrations or 0.1 to 2 M, for example. It should be understood that these concentrations can be adjusted by the skilled person.

In a still further aspect, the invention provides a cell, in particular a eukaryotic cell, containing a polypeptide or a vector as defined above. This cell is advantageously a mammalian cell, in particular an animal or human cell. In particular, it may be a cell of the hematopoietic system, such as a progenitor cell or a strain cell or a lymphocyte cell (T, B). It may also be a cell presenting the antigen such as macrophages or dendritic cells.

Further, the inventors have also shown that the polypeptides of the invention and the polyreactive antibodies are endowed with their own biological properties. The invention demonstrates that these polypeptides (peptide derivatives) or antibodies are capable of inducing a biological effect which is distinct from their ability to vectorise active substances. Unexpectedly, the present invention shows in particular that these antibodies and peptide derivatives are capable by themselves of exerting an antiviral activity on different cell populations and on different types of virus.

The present invention thus also concerns a novel approach to inhibiting viral replication and/or infection in cells. In particular, the present invention concerns the use of particular antibodies or antibody fragments as antiviral agents, in particular to inhibit viral replication and/or infection in cells. The invention also describes a novel method for treating cells to render them more resistant to viral replication and/or infection. The invention also concerns populations of cells treated by antibodies or polypeptides which are less sensitive to viral replication and/or infection. This property can be implemented in vitro, ex vivo or in vivo, optionally in combination with other agents, to reduce infection and development of a virus, in particular infection and/or replication of the human acquired immunodeficiency virus, polio virus, herpes virus or cytomegalovirus, for example.

Thus in a yet still further aspect the invention concerns the use of one or more polypeptides as defined above in preparing an antiviral composition. More particularly the invention concerns the use of one or more antibodies or antibody fragments in preparing an antiviral composition, characterized in that said antibodies or antibody fragments are polyreactive and are capable of binding to a nucleic acid, preferably DNA.

More particularly, an antiviral composition as defined in the invention consists of a composition which is capable of inhibiting infection of a target cell by a virus and/or replication of a virus in a target cell.

As indicated above, this aspect of the present invention stems from the demonstration of the unexpected biological properties of the polypeptides described above and, more generally, of certain polyreactive antibodies, i.e., susceptible of recognising a plurality of antigens, and more specifically having the capability to bind DNA.

In a more particular aspect, then, the invention concerns the use of polyreactive antibodies or antibody fragments, or anti-DNA and penetrating derivative polypeptides, as an antiviral agent.

As indicated above, the polyreactive antibodies or antibody fragments used are preferably capable of recognising at least one proteic antigen of cellular and/or viral origin. More particularly, in addition to DNA, these antibodies or antibody fragments recognise at least one viral antigen such as a viral protein envelope antigen. In one particular implementation, the invention concerns the use of polyreactive antibodies or antibody fragments which are capable of binding a protein or a peptide of the human acquired immunodeficiency virus (HIV). This property can be tested using any conventional immunological technique. Thus HIV proteins or peptides can be immobilised on any suitable support (plate, column, beads, etc.), and to incubate this support with the antibodies. The formation of an antigen-antibody complex can then be detected using any conventional technique (immunofluorescence, enzymatic reaction, etc.). In general, the avidity for HIV proteins or peptides of the anti-DNA antibodies used in the invention is of the order of $10^6$ to $10^7$ M.

Preferably, the antibodies used have the capability of binding HIV Tat and/or rev proteins, more preferably the Tat protein or a peptide of that protein. Particular peptides which can be cited are peptides comprising residues 22–37 and 46–60 of the HIV Tat protein.

In this antiviral application, the antibodies used can be polyclonal or monoclonal antibodies. Polyclonal antibodies can be isolated directly from the serum of subjects (immunised or not immunised, healthy or diseased) by removing blood and isolating antibodies in the presence of immunoadsorbents (for example protein A coupled to a sepharose type support). Polyclonal antibodies which can be used in the invention can in particular be obtained from healthy or diseased animal serum, in particular from rodents, more particularly from mice. They may in particular be autoimmune lupic mice which have high levels of natural antibodies recognising various antigens. Polyclonal antibodies can also be obtained from human serum, for example from patients with disseminated lupus erythematosus, which are also known to present a high natural level of polyreactive antibodies. Concerning monoclonal antibodies, they can be prepared using conventional immunological techniques, by removing splenocytes from immunised or non immunised animals, healty or pathological, fusion with myeloma cells, then clonal dilution and selection of hybridomas producing antibodies. These techniques have been widely documented, in particular by S. L. Morriso and V. T. Oi, in "Advances in Immunology (1989), 44: 65–92; J. G. R. Hurrell, " Monoclonal Hybridoma Antibiotics: Techniques and Applications", CRC Press 1982. These techniques have also been illustrated in the examples. Polyreactive monoclonal antibodies can also be artificially synthesised or humanised from animal monoclonal antibodies.

The antibodies used can be immunoglobulins of different types, in particular IgG or IgM. It should be understood that other types of antibodies can also be used (IgE, IgA, etc.) provided that they have the required properties.

Further, as indicated above, the use of not only intact antibodies but any polypeptide of the invention is also possible, also any fragment of these antibodies which retains the required properties. These fragments can also be (Fab')2, (Fab') or ScFv fragments. These fragments can result from enzymatic antibody digestion, or can be obtained by recombination or by synthesis. The preparation of such fragments (for example by enzymatic treatments) has been widely documented in the literature and can thus be carried out by the skilled person using simple routine operations starting from antibody preparations.

As indicated above, this aspect of the present invention stems in part from the discovery of the antiviral properties of such polypeptides, antibodies and fragments, in particular their ability to inhibit viral replication in a target cell or infection of a target cell by a virus. The term "infection" means penetration of the virus or viral genome into the target cell, and the term "replication" essentially means replication of the viral genome in said target cell.

The present invention can be employed to inhibit the cycle of different viruses, more particularly a RNA virus (retrovirus) or a DNA virus. Further, it may be a virus with tropism for man or for different animals, in particular mammals (dogs, cats, rabbits, cattle, etc.) More preferably, the present invention can inhibit a virus such as the human immunodeficiency virus (HIV), polio virus, herpes virus or cytomegalovirus (CMV).

A particular implementation of the invention comprises the use of one or more polyreactive antibodies or fragments of such antibody for preparing a composition intended to inhibit infection of a target cell by HIV and/or replication of HIV in a target cell, characterized in that said antibodies or antibody fragments have the ability to bind DNA. More preferably, the antibodies used also have the ability to bind a protein or a peptide of the human acquired immunodeficiency virus. More particularly, the invention can be used to inhibit infection and/or replication of different strains of HIV, in particular HIV-1 and HIV-2.

More particularly, the invention concerns the use of one or more polypeptides as described above to prepare a composition intended to inhibit viral replication and/or infection.

Within the context of the invention, the term "target cell" means any cell which is naturally susceptible of being infected by a virus, preferably susceptible of enabling replication of the virus. In the case of HIV, the target cells are constituted by cells of the immune system, in particular lymphocytic cells. More specific examples of HIV target cells are T lymphocytes, in particular auxiliary T lymphocytes (CD4+). Other HIV target cells for the invention are more generally constituted by peripheral mononuclear cells, in particular human (PBMC). Regarding the polio virus, an example of target cells are epithelial cells. In general, the present invention can be employed to interfere with the development of a virus in any type of target cell for the antibodies used.

Advantageously, a polypeptide of the invention is derived from recombinant ScFv fragments, capable of reacting with DNA or with other anionic or cationic macromolecules, in particular heparin and heparin sulphate, and obtained from lymphocytes originating from normal patients or patients with different diseases in particular disseminated lupus erythrematosus.

The mechanism(s) for the action of the compounds of the invention still have to be elucidated. In this respect, a series of recent results, in particular for the herpes virus, in particular the human herpes virus for example the type 1 herpes simplex virus or cytomegalovirus (CMV) appears to indicate that the peptides of the invention affix to cellular receptors used by the virus themselves to penetrate into the host cells. Fixing of peptides on these receptors is followed by internalisation of the peptide-receptor complexes, which results in a reduction in the number of cellular receptors remaining available to fix the virus. This reduction sometimes appears to be especially significant as in the case of CMV. However, other mechanisms, in particular on the level of the nucleus, could also be involved in the unexpected properties of these antibodies and derivatives.

Advantageously, the antiviral activity of the polypeptides means a significant reduction in replication or infection. Advantageously, the inhibition produced by the polypeptides or antibodies of the invention corresponds to a reduction by a factor of at least 1.5 with respect to the level of infection and/or replication in the same cells or cell populations in the absence of treatment. More preferably, inhibition corresponds to a reduction by a factor of at least 4. This inhibition can be quantified, for example by measuring the viral plaques, the levels of viral antigens present in the cells, cell viability, etc . . . In a particular implementation, the inhibition efficacy is evaluated by measuring the levels of viral antigens such as p24 and/or gp120 antigens, for HIV.

In a particular implementation, the invention concerns the use of antibodies or polypeptides to induce an inhibition of a factor of at least 2 in viral replication in the target cells.

In a first implementation, the invention comprises using a single type of polypeptide or antibody or antibody fragment as defined above. As illustrated in the examples, by using a single compound it is in fact possible to inhibit HIV-1 replication in target cells by a factor of more than 10, in particular of the order of 100. The use of a single compound can also produce an inhibition by a factor of more than 2 in the replication of type-1 polio virus in target cells.

Further, a pronounced anti-herpetic reaction has been observed for certain antibodies and peptides of the invention. It is important to indicate that this action is also observed with HSV-1 thymidine-kinase$^-$ (TK$^-$) on which acyclovir has no effect.

Further, a pronounced anti-CMV action has also been observed, in particular with the K19-pF4-1 polypeptide. In a series of experiments, it has been demonstrated that K19-pF4.1 inhibited the infection of cells by CMV by almost 100%. It is important to note that even the synthesis of early antigens was completely inhibited (detection both by immunofluorescence and radiolabelling, followed by immunoprecipitation).

In a further implementation, the invention comprises the use of a plurality of polypeptides, antibodies and/or antibody fragments as defined above. As illustrated in the examples, certain of these compounds, in combination, can exert a synergistic inhibition effect on viral replication in target cells. Thus, unexpectedly, certain antibodies, alone, have a moderate inhibiting activity but in combination induce an inhibition of HIV-1 replication in target cells by a factor of more than 10, in particular of the order of 100.

In a further implementation, the invention also comprises the use of one or more polypeptides, antibodies and/or antibody fragments as defined above in combination with one or more antiviral agents. Examples of such antiviral agents are AZT, DDI and antiproteases. In this regard, the present application also concerns a product comprising:

one or more polypeptides, antibodies and/or antibody fragments as defined above; and an antiviral agent; for simultaneous, separate or intermittent use.

The present invention can be used to inhibit viral replication and/or infection in vitro, ex vivo or in vivo.

For in vitro or ex vivo use, the target cells, or a cell composition comprising target cells, are generally incubated in the presence of compounds as defined above. The doses of the polypeptides, antibodies or antibody fragments used are generally in the range about 1 to 500 µg per $10^6$ cells, preferably about 1 to 100 µg/$10^6$ cells. These doses can of course be adapted by the skilled person without difficulty. Incubation is carried out in any suitable cell culture medium, and under the normal temperature conditions (for example between ambient temperature and about 37° C.). The media used are any mammal cell culture media known to the skilled person, such as RPMI, DMEM, MEM, etc . . . Incubation can be carried out using any suitable apparatus such as a dish, flask, ampoule, pouch, tube, syringe, etc., preferably under sterile conditions. Advantageously, incubation is carried out for a period in the range about 1 hour to about 5 days, depending on the use and aim. As an example, cells can be incubated for a period in the range from about 1 hour to about 12 hours. The incubated cells can then be administered to a subject (autologous), and the subject can also receive one or more administrations of antibodies or antibody fragments.

For in vivo use, the compounds can be administered by different routes, such as systemic, intramuscular, or subcutaneously, for example. Preferred routes are systemic (in particular i.v.) and sub-cutaneous. The doses used can also be adapted by the skilled person as a function of the stage of the subject, the desired aim and the number and/or frequency of administrations.

Preferably, the invention is employed to inhibit viral infection or replication in target cells ex vivo. To this end, target cells are removed from a subject (PBMC, for example), incubated ex vivo with compounds as defined above (for example for 1 to 6 hours, at 37° C., in a sterile pouch), then re-administered to the subject. The subject can also receive one or more administrations of the compounds, optionally in combination with one or more other antiviral agents. The compounds or compositions as described above are particularly suitable for preventive use, i.e., to inhibit viral replication or infection in healthy or seropositive subjects but who have not developed the symptoms of the disease. The invention can also be used as a maintenance treatment, used alone or in combination with other antiviral agents, as explained above.

The invention thus also concerns a method for improving the efficacy of antiviral agents comprising the combined use of polypeptide, antibody or antibody fragments as defined above.

The invention also concerns a method for modifying a cell with the aim of reducing infection of this cell by a virus and/or replication of a virus in this cell (i.e., to improve viral resistance of this cell), comprising bringing said cell into contact with one or more polypeptides, antibodies or antibody fragments as defined above. The invention also concerns any population of cells incubated in the presence of polypeptides, antibodies or antibody fragments as defined above. More particularly, such populations can be PBMC cells or other cells of the immune system, optionally packaged in a sterile container. Preferably, such a cellular composition generally comprises $10^5$ to $10^8$ cells. These cellular compositions can be used to study the viral cycle, to search for inhibiting compositions or associations of inhibiting compounds, or optionally to reduce the risks and effects of a viral infection in vivo after administration.

The invention also concerns a pharmaceutical composition comprising, in association with a physiologically acceptable vehicle, a vector as defined above in which the substance is an active principle of a drug.

The invention still further concerns a vaccine comprising, in association with a physiologically acceptable vehicle, a vector as defined above in which the substance is an antigen.

The present invention will now be described in more detail using the following non limiting examples which are provided by way of illustration.

BRIEF DESCRIPTION OF THE DRAWINGS

FIG. 2: Peptide sequence (SEQ ID NOS: 25–29) of the variable regions of the heavy chain of penetrating monoclonal antibody. The CDR regions are shown. "–" means identical amino acids.

FIG. 3: Sequence for CDR2 (SEQ ID NOS: 30–32) and CDR3 (SEQ ID NOS: 33–35) regions of the VH domains in cells penetrating anti-DNA antibody.

FIG. 7: Polyfection of 3T3 cells by the K19-P3 peptide as a function of incubation time of the cells with the complex.

FIG. 8: Polyfection of 3T3 cells in the absence (FIG. 8a) or presence (FIG. 8b) of a facilitator agent: glycerol.

Figure 1:
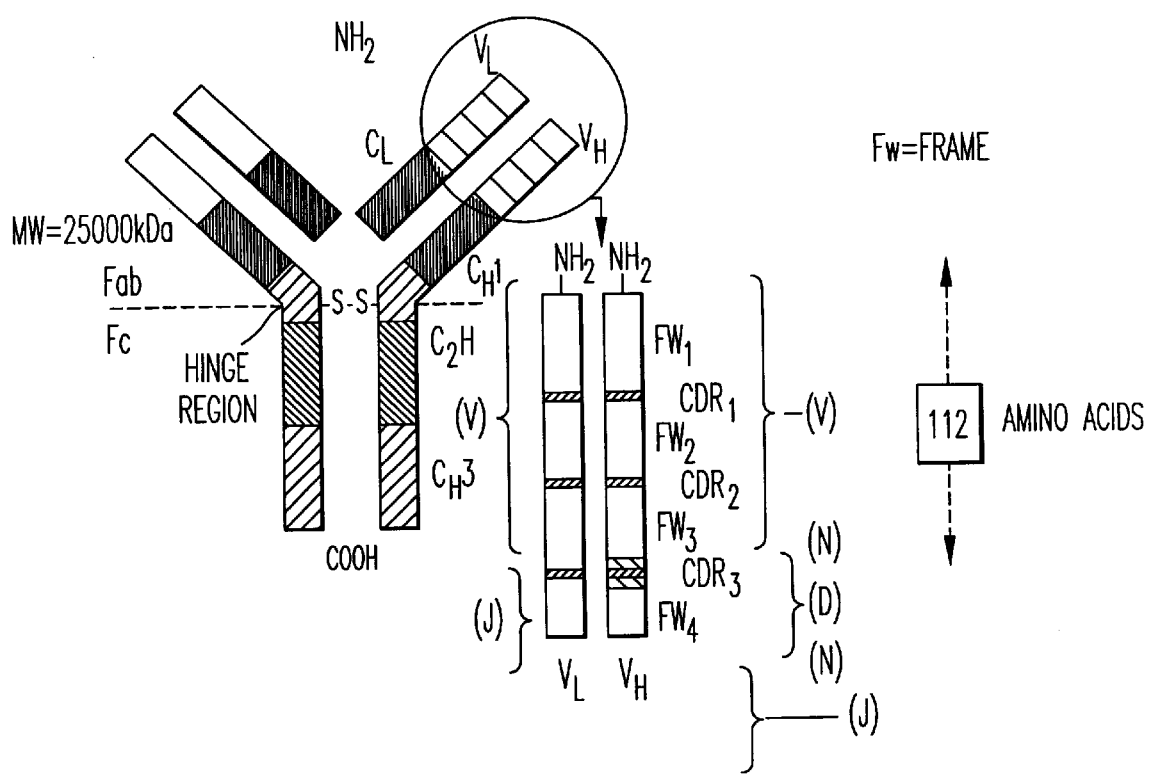
FIG. 1: Diagram of the structure of an antibody.

11A and 11B: Measurement of infectious titers on day 13 in two series of independent experiments (experiments III and V).

11C: Quantification of p24 antigen in supernatants of cultures inoculated with $10^2$ dilution on day 9. (experiment V).

Figure 12:
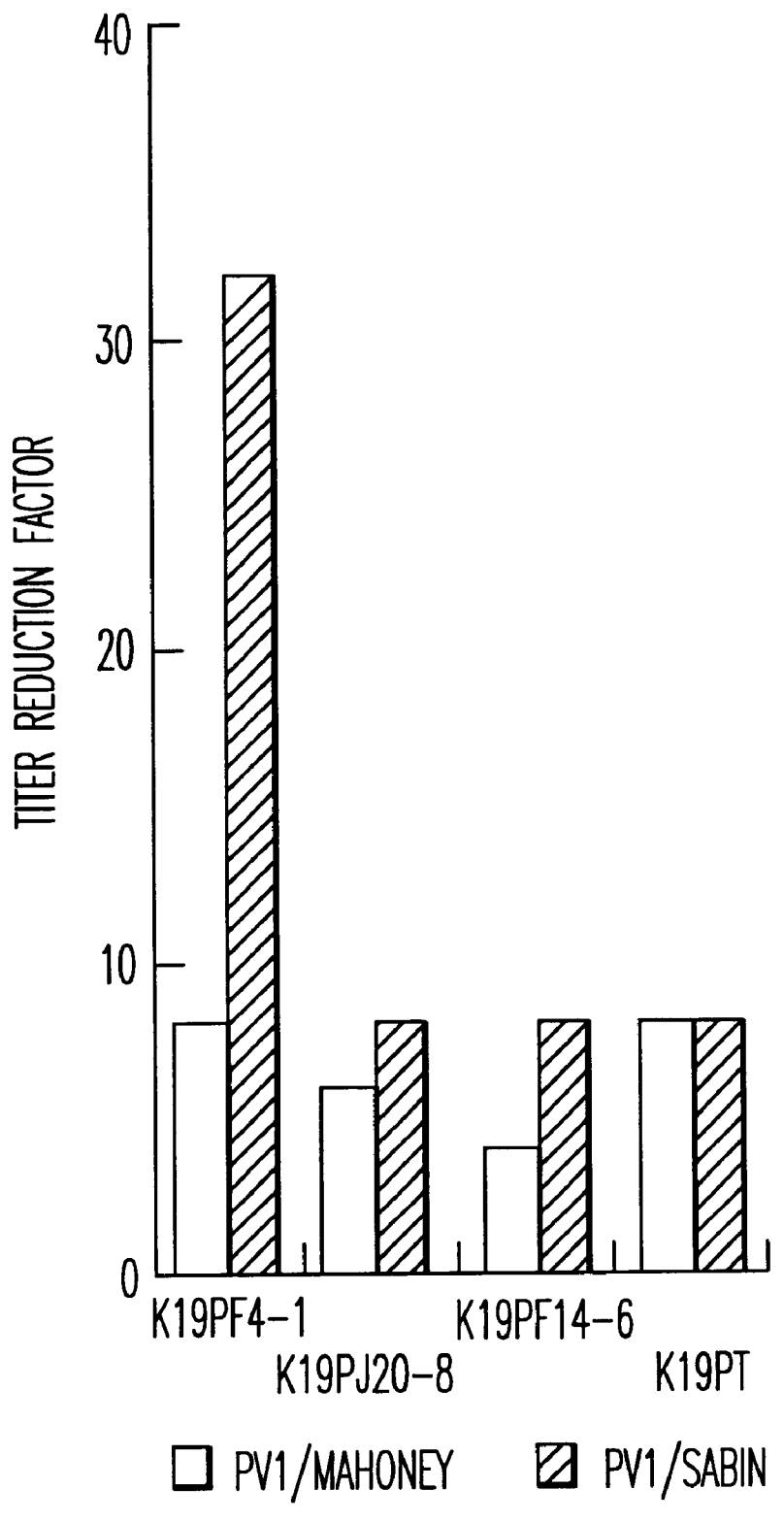

FIG. 12: Inhibition of replication of polio virus by polypeptides by measuring the viral titer reduction factor on day 5.

Solid bars: wild-type polio virus strain.

Hatched bars: attenuated polio virus strain.

FIG. 13: Demonstration of inhibition of CMV protein synthesis after treatment with K19-pF4.1 (PL) polypeptide, P3 peptide, or no peptide (NT), before viral infection (13a, 13b), during viral infection (13c) or after viral infection (13d). It was revealed using an anti-pp150 antibody (for late proteins), anti-pp65 (for early proteins) and anti-IE (for very early proteins).

DETAILED DESCRIPTION OF THE INVENTION

Method and Apparatus
Mice and Cell Lines:

BALB/c (NZB×NZW) F1 mice were kept in the animal house at the Institut Pasteur. Cells from different species and from different tissues were used: PtK2 cells (kidney fibroblasts), GMA-32 cells (hamster lung), 3T3 cells (mouse embryo fibroblasts), CCL39 cells (hamster fibroblasts), HeLa cells (human cervical carcinoma), VERO cells (monkey kidney), HEp-2 cells (human larynx carcinoma), JURKAT cells and CEM cells (human T lymphoblasts) all available from the ATCC Collection. These different cell types were cultivated in RPMI medium or in DMEM medium containing 10% of inactivated foetal calf serum and supplemented with L-glutamine, sodium pyruvate and non-essential amino acids and antibiotics (complete culture medium) at 37° C. in a moistened atmosphere containing 5% $CO_2$.

Monoclonal Antibodies

The preparation and isolation of monoclonal antibodies J20.8, F4.1 and F14.6 have been described in French patent application FR-9508316. These antibodies are polyreactive anti-DNA antibodies and also recognise different antigens such as peptides 22–37 and 46–60 from the Tat protein. These antibodies are murine IgG2a cells. The anti-Tat antibody used is a monoreactive murine IgG1 monoclonal antibody recognising the Tat protein of HIV-1.

These antibodies were purified on a protein A sepharose column (Ey et al., Immunochemistry 15 (1978) 429). The polyreactivity of these purified antibodies as regards double stranded DNA and other antigens was tested using ELISA employing the methodologies described in the literature (Guilbert et al., J. Immunol. 128 (1982) 2779).

Peptide Synthesis

The peptides were synthesised using techniques which are known to the skilled person. Thus the peptides were produced by solid phase synthesis on Fmoc resin. Trifluoro-acetic acid (TFA) was used for cleavage and the peptides were purified on a semi-preparative HPLC-RPC5 column (Eurosil Bioselect 5μ, 300 A (1;6×25 cm) and eluted at 1.1 ml/min with a 0.1% TFA solution and an acetonitrile gradient (10–70%). The lyophilised peptides were dissolved in 0.15 mM NaCl and sterilised with a 0.22 μm filter. To determine the peptide concentration, aliquots were hydrolysed at 110° C. in the presence of 6N HCl—2% phenol then analysed using a Beckman 6300 amino acid analyser.

Viral Strains

The experiments described below were carried out using the following viral strains: HIV-1 BX08 strain (primary isolate, sub-type B); HIV-1 Lai strain; polio virus type 1 (wild type PV1 Mahoney strain and attenuated Sabin PV1); cytomegalovirus Ad169 strain and Herpes Virus Simplex type I.

EXAMPLES

1. Sequencing of Monoclonal Antibodies

The nucleotide sequence of the VH and VL regions of monoclonal antibodies J20.8, F4.1 and F14.6 were determined. To this end, total RNA was extracted from hybridoma cells using the guanidine thiocyanate technique (Schwartz et al., Biol. Cell. 73 (1991) 7) then separated by formaldehyde/agarose gel electrophoresis. The messenger RNAs obtained was then transformed into complementary DNA using a reverse transcriptase kit (Life Technologies, Eragny, France) and used as a primer in amplification reactions (PCR) using Taq DNA polymerase (Boehringer, Mannheim, Germany) following the manufacturer's instructions. The oligonucleotide primers used to generate the complementary DNA were:

firstly, a primer corresponding to the conserved sequences of IgG2a immunoglobulins:
5'-GTTCTGACTAGTGGGCACTCTGGGCT (SEQ ID No 11)

and secondly, four primers for the VH region:
5'-GAGGTTCAGCTCGAGCAGTCTGGGGC (SEQ ID No 12)
5'-GAGGTGAAGCTCGAGGAATCTGGAGG (SEQ ID No 13)
5'-GAAGTGCAGCTCGAGGAGTCTGGGG (SEQ ID No 14)
5'-GAGGTTCAGCTCGAGCAGTCTGGAGC (SEQ ID No 15)

The PCR amplification products were then purified using a Geneclean kit (Bio 101, Vista, Calif.). Chemical sequencing was carried out by Genome Express. (Grenoble, France). The nucleotide sequences were analysed using GENBANK and EMBL databases held at the Institut Pasteur (Information Science Unit) using GCG sequence analysis software (GCG) (Devereux J., "The GCG Sequence Analysis Software Package", 1989), and the corresponding amino acid sequences were deduced.

The sequence for the VH regions of these antibodies is shown in FIG. 2. Alignment of these sequences enables the CDR regions (CDR1, CDR2 and CDR3) present in these sequences to be localised. This alignment also demonstrates the existence of a substantial structural homology between the CDR2 regions and the common structural characteristics between the CDR3 regions, in particular the presence of basic residues (arginine and lysine). The sequences for the CDR2 and CDR3 regions of other antibodies are shown in FIG. 3.

2. Construction of Penetrating Polypeptides

Starting from the sequences shown in FIG. 1, different polypeptides comprising all or a portion of the CDR3 region and/or the CDR2 region of the antibodies were prepared. Synthesis was carried out by peptide synthesisers (see Method and Apparatus section). The following polypeptides were synthesised, where m is 1 or 0:

CDR3:
SEQ ID no 1:
(Thr)$_m$-(Arg)$_m$-(Gln)$_m$-Lys-Tyr-Asn-Lys-Arg-Ala-(M-D-Y-W-G-Q-G-T)$_m$

A variation of this sequence is, for example the sequence TRQKYNKRA(MDYWGQGT)$_m$. (SEQ ID NO:16) A further variation (functional homologue) is, for example, the sequence Ala-Arg-Gln-Lys-Tyr-Asn-Lys-Arg-Ala-Met-Asp-Tyr (SEQ ID no 8).

SEQ ID no 2:
(Thr)$_m$-(Arg)$_m$-(Gln)$_m$-Lys-Tyr-Gly-Lys-Arg-Gly-(M-D-Y-W-G-Q-G-T)$_m$

A variation of this sequence is, for example the sequence TRQKYNKKRG(MDYWGQGT)$_m$. (SEQ ID NO:17)

SEQ ID no 3:
(Thr)$_m$-(Arg)$_m$-(Gln)$_m$-Ala-Arg-Ala-Thr-Trp-Asp-Trp-(F-A-Y-W-G-Q-G-T)$_m$

A variation of this sequence is, for example the sequence TRGARATWDW(FAYWGQGT)$_m$. (SEQ ID NO:18)

In sequences 1 to 3 above, MDYWGQGT=Met-Asp-Tyr-Trp-Gly-Gln-Gly-Thr (amino acids 11–18 of SEQ ID NO:16) and FAYWGQGT=Phe-Ala-Tyr=Trp=Gly-Gln-Gly-Gly-Thr (amino acids 11–8 of SEQ ID NO:18). Further, the formula (a-b-c)$_m$ means that a single, some or all of the residues mentioned in brackets are present or not present.

SEQ ID no 4:
(Val)$_m$-(Ala)$_m$-Tyr-Ile-Ser-Arg-Gly-Gly-Val-Ser-Thr-Tyr-Tyr-Ser-Asp-Thr-Val-Lys-Gly-(Arg)$_m$-(Phe)$_m$-(Thr)$_m$ (CDR2 (1)). A variation of this sequence is, for example, the sequence VAYISRGGVSTYYS-DTVKGRF (SEQ ID NO:19) or VAYISRG-GVSTYYSDTVKGRFT. (SEQ ID NO:20)

SEQ ID no 5:
(Val)$_m$-(Ala)$_m$-Tyr-Ile-Ser-Arg-Gly-Gly-Gly-Ile-Phe-Tyr-Tyr-Glu-Asp-Ser-Ile-Lys-Gly-(Arg)$_m$-(Phe)$_m$ (CDR2 (2)). A variation of this sequence is, for example, the sequence VAYISRGGIFYYQDSIKGRF. (SEQ ID NO:21)

SEQ ID no 6:
(Val)$_m$-(Ala)$_m$-Ala-Ile-Ser-Arg-Gly-Gly-Gly-Tyr-Ser-Tyr-Tyr-Leu-Asp-Ser-Val-Lys-Gly-(Arg)$_m$-(Phe)$_m$-(Thr)$_m$-(Ile)$_m$ (CDR2(3)). A variation of this sequence is, for example, the sequence VAAIS-RGGGYSYYLDSVKGRFTI. (SEQ ID NO:22)

CDR2–3:
SEQ ID no 7 (p3 or Pf4.1 peptide):
Val-Ala-Tyr-Ile-Ser-Arg-Gly-Gly-Val-Ser-Thr-Tyr-Tyr-Ser-Asp-Thr-Val-Lys-Gly-Arg-Phe-Thr-Arg-Gln-Lys-Tyr-Asn-Lys-Arg-Ala. A variation of this sequence is, for example, the sequence VAYISRGGVSTYYS-DTVKGRFTRQKYNKRAVAY. (SEQ ID NO:23)

Functionalised CDR2–3:
Biotinyl-Val-Ala-Tyr-Ile-Ser-Arg-Gly-Gly-Val-Ser-Thr-Tyr-Tyr-Ser-Asp-Thr-Val-Lys-Gly-Arg-Phe-Thr-Arg-Gln-Lys-Tyr-Asn-Lys-Arg-Ala— (corresponding to the sequence SEQ ID no 7).

Cys-Val-Ala-Tyr-Ile-Ser-Arg-Gly-Gly-Val-Ser-Thr-Tyr-Tyr-Ser-Asp-Thr-Val-Lys-Gly-Arg-Phe-Thr-Arg-Gln-Lys-Tyr-Asn-Lys-Arg-Ala— (SEQ ID no 9).

An active group (SH) was introduced into sequence SEQ ID no 9 via cystein to enabling coupling to another substance.

Functionalised CDR2:
Biotinyl-VAYISRGGVSTYYSDTVKGRFT (Biotinyl-Val-Ala-Tyr-Ile-Ser-Arg-Gly-Gly-Val-Ser-Thr-Tyr-Tyr-Ser-Asp-Thr-Val-Lys-Gly-Arg-Phe-Thr), corresponding to sequence SEQ ID no 4.

Functionalised CDR3:
Biotinyl-Ala-Arg-Gln-Lys-Tyr-Asn-Lys-Arg-Ala-Met-Asp-Tyr (corresponding to sequence SEQ ID no 8).

3. Study of the Penetration of Polypeptides Into Cells

Cultured PtK2 fibroblasts seeded the day before in an amount of $5 \times 10^4$ cells per well onto glass sheets, are incubated at 37° C., 1–18 hours in complete RPMI 1640 culture medium (or DMEM) (10% foetal calf serum, 2 mM L-glutamine and 1 mM of sodium pyruvate) containing a biotinylated polypeptide of the invention (5–20 μg/ml) The cells were then washed with PBS and fixed with 2% of p-formaldehyde at 4° C. for 10 minutes then washed with PBS.

The cells were then incubated with a solution of streptavidin conjugated with 5 μg/ml of peroxidase in PBS for 30 minutes, then washed with PBS and incubated in the peroxidase cytochemical substrate (diaminobenzidine+$H_2O_2$) After washing, the cells were examined microscopically.

The results obtained show that after 1 hour of culture, the polypeptides comprising all or a portion of a CDR3 were visible by peroxidase coloration in the cytoplasm of all of the cells and in the nucleus of a large number of cells. The results also show that the polypeptide CDR2–3 (in particular the pF4.1 polypeptide with sequence SEQ ID no 7) penetrated massively and rapidly into the cells and most reached the nucleus of said cells. These results thus show that it is possible to generate polypeptides with a high cell penetration capacity from a CDR3 type fragment.

4. Cell Penetration of Polypeptide-streptavidin Vectors Coupled to Enzymes

This example illustrates how the polypeptides of the invention can be coupled to an active substance and used to transport said substance into cells.

The vectors were prepared by incubating 1.4 µg of biotinylated CDR2–3 polypeptide (pF4.1) with 10 µg of streptavidin conjugated with peroxidase or with alkaline phosphatase in a volume of 10 µl for 15 minutes at laboratory temperature. The mixture was then diluted in 0.5 ml of complete culture medium before being deposited on the cells in culture. After 2 hours of culture, the cells were washed with PBS, fixed with p-paraformaldehyde, washed then incubated in the peroxidase cytochemical substrate (diaminobenzidine+$H_2CO_2$) or that of alkaline phosphatase (Naphthol AsMx+Fast Red tetrazolium salt).

The results obtained show that the corresponding enzymes were detected in the cytoplasm of all of the cultured cells and weakly to intensely in the majority of the cell nuclei. In contrast, no intracellular coloration was observed when the cells were incubated in the presence of streptavidin coupled with peroxidase, streptavidin coupled with alkaline phosphatase or with streptavidin or the enzymes in their native forms.

5. Construction and Activity of a Polypeptide Comprising Supplemental Lysine Residues A CDR2–3-PL19 (polylysine) (also termed K19-P3 or K19-pF4.1) was synthesised and purified (ALTERGEN). The sequence of the polypeptide is as follows:

(NH2-(K19)-VAYISRGGVSTYYSDTVKGRFTRQKYNKRA-COOH) SEQ ID no 10.

CCL39 cells (hamster fibroblasts) ($5 \times 10^4$ cells) were placed in 24 well culture plates for 18 hours before transfection in MEM+10% FCS (foetal calf serum) culture medium. Transfections were carried out in MEM+10% FCS with no other auxiliary agent (CHLOROQUINE). The peptide-PL and free polylysine PL (corresponding to 19 lysines) were complexed with the pCMVLUC plasmid (respectively 24 µg and 70 µg per 6 µg of plasmid) for 30 minutes. The complex was then added dropwise to the CCL39. After incubating for 5 hours, the medium was replaced with fresh medium. Luciferase expression was assayed 24 hours later. The cells were washed twice with PBS. After washing, the cells were lysed with 100 µl of lyse buffer (PROMEGA) for 10–15 minutes. The cells were then centrifuged for 7 minutes at 4° C. to remove cellular debris. 20 µl of this lysate was mixed with 100 µl of luciferase buffer (PROMEGA). The relative luciferase units (RLU) were recorded on a LUMAT LB9501 (BERTHOLD) The protein concentration was determined using a BIORAD PROTEIN ASSAY-1 kit and the amount of luciferase in each sample was normalised per mg of protein, each transfection being carried out three times.

Figure 5:
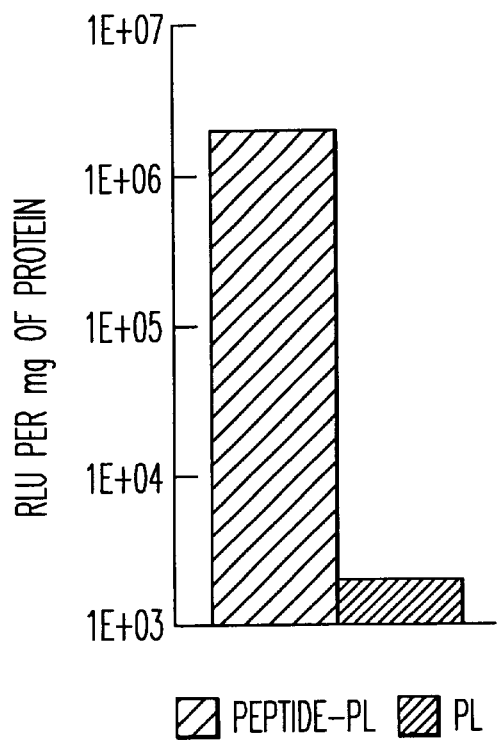
FIG. 5: DNA transfection activity of the CDR2–3-PL19 peptide in CCL39 cells.

The results obtained are shown in FIG. 5. They show that in complete medium and with no auxiliary agent, the peptide-PL transfects with an efficacy of $2 \times 10^6$ RLU/mg of proteins, i.e., about 1000 times more than polylysine alone and more than a peptide recently described (Wadhwa et al., Bioconjugate Chem. 1997, 8:81–88), but where the activity was dependent on the presence of 100 µM of chloroquine.

Transfecting cells with the CDRK19-P3 polypeptide is thus particularly advantageous since it can be carried out in a complete culture medium and in the absence of auxiliary agent. Current transfection systems using polylysine all require the addition of an auxiliary agent, usually chloroquine which is toxic for the cells. This chloroquine prevents degradation in the lysosomes of conugate-polylysine complexes internalised by the conventional endocytosis route.

In contrast, the present invention does not require the use of such auxiliary agents.

6. Polyfection of 3T3 Cells With the K19-P3 Peptide

This example illustrates the transfer properties of nucleic acids of the peptides of the invention in 3T3 cells.

3T3 cells ($8 \times 10^4$ cells) were distributed into 24 well plates the day prior to transfection. Polyplexes between the pCMV LUC plasmid and the K19-P3 peptide or control peptides CW-K19 and K19 were prepared by incubating 3 µg of plasmid in 50 µl of 0.15 M NaCl for 20 minutes at 20° C., with different quantities of peptide. More particularly, the polyplexes were produced in stoichiometries of 0.05 to 1.4 nmoles of peptides per µg of DNA.

Shortly before transfection, the cells were washed, then incubated for different periods with 0.5 ml of complete culture medium. The polyplexes were added to the cells for 1 h 15, 2 h 30, 5 h 30 and 24 h at 37° C. in a moist atmosphere (92% air, 8% $CO_2$). The medium was eliminated and the cells incubated again for 24 hours at 37° C. in 1 ml of fresh medium. Each experiment was carried out at least three times. The luciferase activity was determined as for Example 5.

Figure 6:
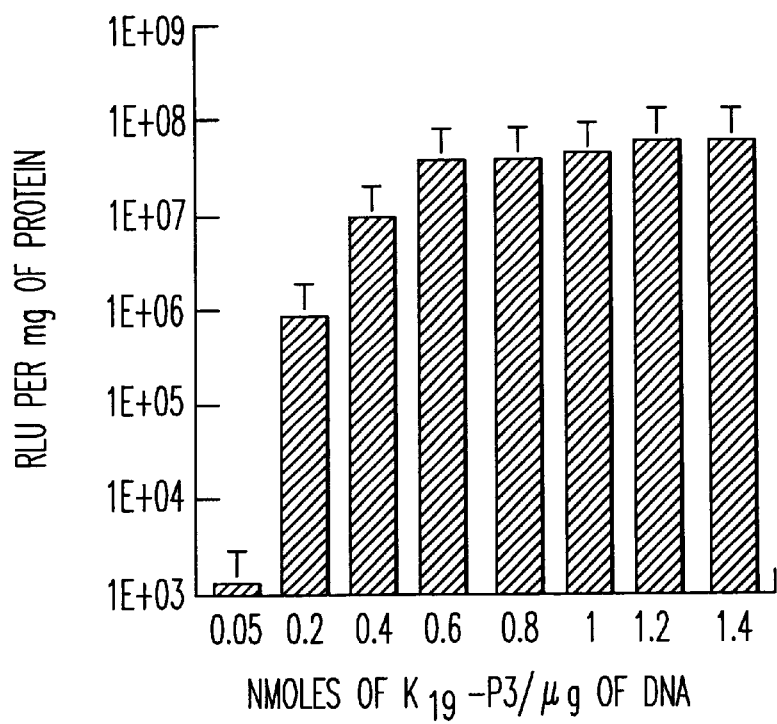
FIG. 6: Polyfection of 3T3 cells by the K19-P3 peptide at different peptide/plasmid ratios.

The results obtained are shown in FIGS. 6 and 7.

FIG. 6 shows an increase in luciferase expression correlated with an increase in the concentration of peptide, the maximum activity being observed at a concentration of 0.6 nmoles of peptide/µg of DNA. This concentration corresponded to a charge ratio of R=4.4. At higher concentrations, expression remained constant.

FIG. 7 also shows that, at a charge ratio R of 4.4, exposure of cells for 24 hours to the polyplex did not induce any toxicity. After incubating for 5h30, the luciferase activity which was measured was $2-3 \times 10^7$ RLU/mg of protein for the K19-P3 peptide. Transfection after incubating for 24 h was increased by a factor of about 1.3 with respect to incubating for 5 h30.

7. Polyfection in the Presence of Glycerol

This example shows that transfection efficacy can be improved using a composition comprising a peptide of the invention and a stabiliser such as glycerol.

In this example, transfections were carried out on 3T3 cells and CCL39 cells, as described in Example 6, in a complete medium containing or not containing glycerol (0.23 M) in a peptide/DNA charge ratio of 2.2 (incubation for 5 h 30 at 37° C.).

Further, by way of comparison, transfection was carried out in the presence of polyethylene immine (PEI), 25 kDa (Aldrich, St Louis, Mo.) in a charge ratio of 2.2 in the presence of glycerol and 5 in the absence of glycerol.

Figure 9A:
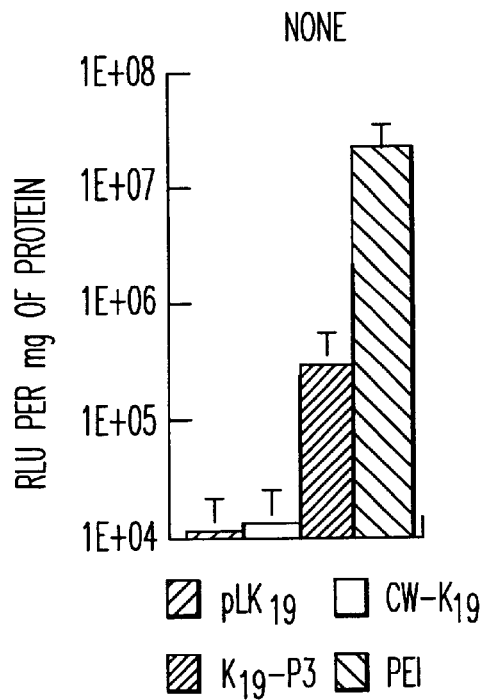
FIG. 9: Polyfection of CCL39 cells in the absence (FIG. 9a) or presence (FIG. 9b) of a facilitator agent: glycerol.
Figure 9B:
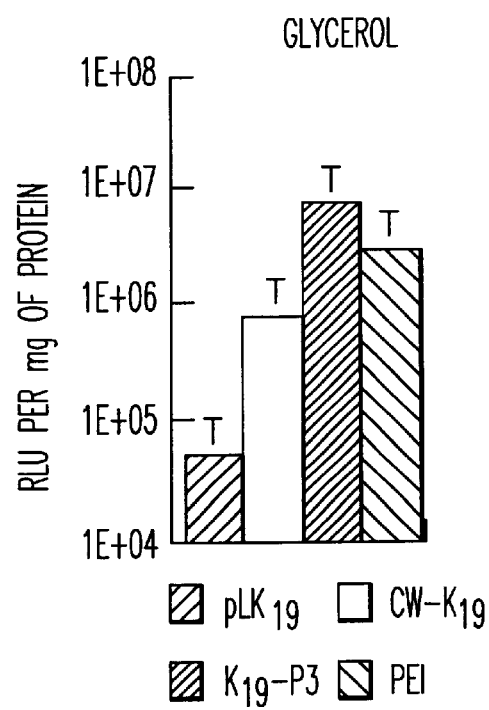

The results obtained are shown in FIGS. 8 and 9.

These results show that glycerol (0.23 M) induces an increase in polyfection (determined by measuring the luciferase activity) by a factor of more than 5, possibly up to 40. Thus in CCL39 cells (FIG. 9), an increase by a factor of 38 was demonstrated, illustrating the importance of a composition of the invention comprising glycerol, in particular for transfecting cells which are difficult to transfect. Further, similar results were obtained by varying the concentration of the glycerol in the medium, up to a value of 1.15 M.

The results shown in FIGS. 8 and 9 also show that the transfection efficacy of the peptides of the invention, which are non toxic and of a simple, defined structure, are higher than 25kDa PEI in the presence of glycerol, both for 3T3 cells and for CCL39 cells.

8. Use of P polypeptide as an Immunoadjuvant

The vector was formed by incubating 14 μg of biotinylated CDR2–3 polypeptide+40 μg of streptavidin conjugated with peroxidase (Sigma) for 15 minutes then diluting in 0.1 ml of PBS before being injected into each mouse. Injection was via the pads. The control mice received 40 μg of streptavidin conjugated with peroxidase in 0.1 ml of PBS.

Figure 4A:
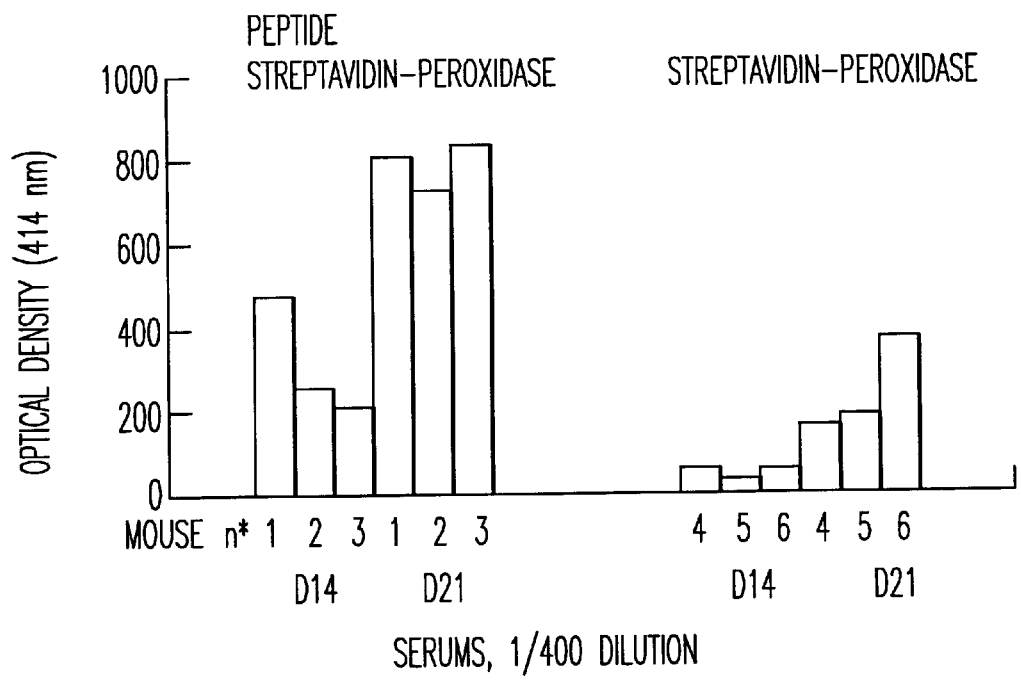
FIG. 4: ELISA demonstration of the in vivo adjuvant effect of the polypeptides of the invention.
Figure 4B:
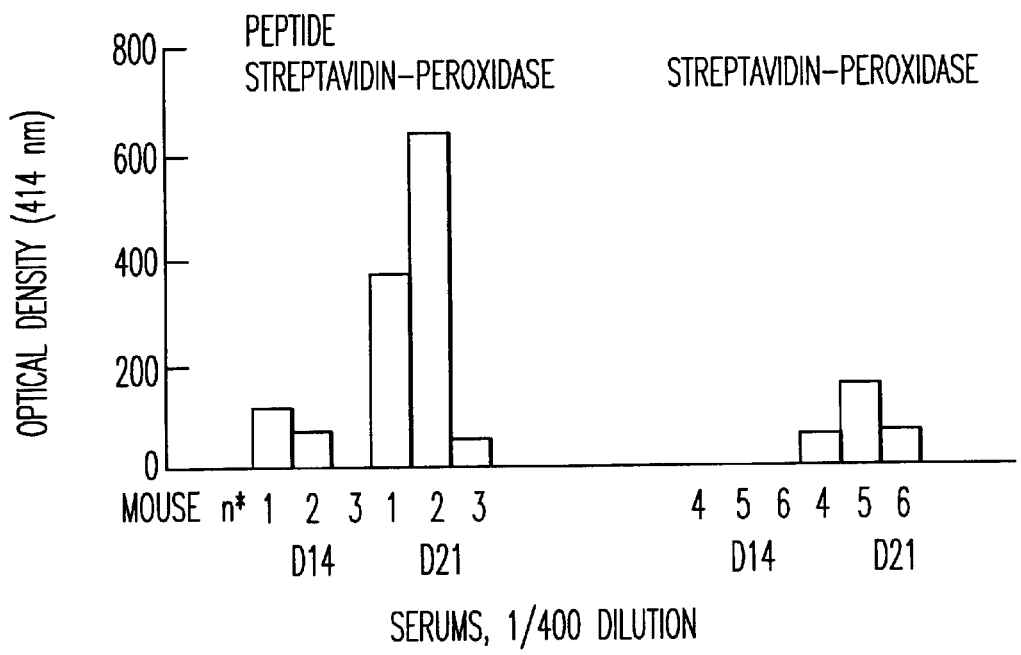

The mice were bled every week. A repeat injection was carried out under the same conditions one month after the first injection. An ELISA test showed that the mice which had received the CDR2–3-streptavidin conjugated with peroxidase complex responded with anti-streptavidin and anti-peroxidase IgG antibodies, but with very few IgM, with substantially higher values than those which had received streptavidin conjugated with peroxidase alone and from the $14^{th}$ day (FIG. 4). The repeat injection caused an increase in the antibody titer in the two groups, but the values were always higher in the group which had received the complex. On the basis of these results, it thus appears that under the test conditions, the polypeptides of the invention are capable of increasing the titer of antibodies directed against a given antigen by a factor of at least 4 to 8.

The same experiments can be reproduced using not a protein as the antigen but a nucleic acid coding for said antigen. Further, these experiments can also be repeated under the same conditions with a polypeptide comprising supplemental basic residues, in particular a polylysine.

9. HIV Inhibition

This example illustrates the antiviral properties of polyreactive antibodies of the invention on HIV-1 Lai strain.

Cells

The target HIV cells used were human peripheral blood mononuclear cells (PBMC). These cells were obtained from healthy subjects using any technique which is known to the skilled person (Ficoll gradients, leukapheresis, etc.). The PBMC cells were activated by phytohemagglutinin for about 3 days and kept in culture at 37° C. in a $CO_2$ atmosphere in the presence of interleukin-2.

Assay of p24 Antigen

The p24 protein was assayed in cell culture supernatants using an ELISA test employing a commercially available kit (Diagnostic Pasteur).

Figure 10:
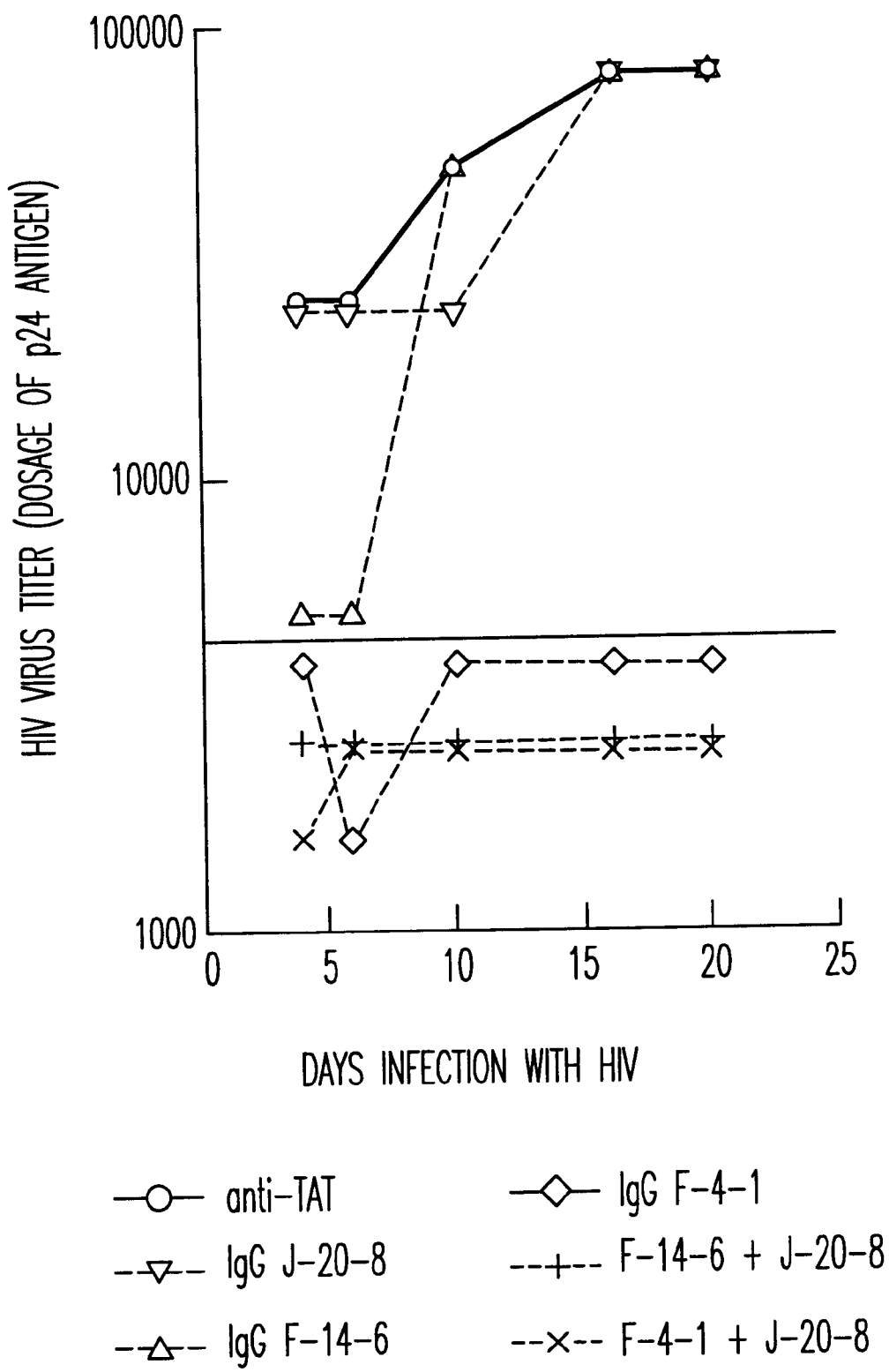
FIG. 10: Infectious titers and determination of the p24 antigen of HIV1 produced in a culture medium for human circulating mononuclear cells (PBMC) treated with different preparations of antibody and infected with HIV1 Lai. Average values for three independent experiments.

Human peripheral blood mononuclear cells (PBMC), after activation in phytohemagglutinin, were incubated at different concentrations with the three antibodies J20-8, F14-6 and F4-1 for 4 hours at 37° C. After eliminating the antibodies, the cells were infected with successive dilutions of HIV-1 Lai (1 hour at 37° C.), washed, incubated with fresh culture medium in the presence or not in the presence of antibody and the supernatant was examined every 3 or 4 days for the presence of the P24 antigen of HIV-1 to evaluate the level of viral replication in treated or untreated cells. The results of these titrations of HIV-1 Lai on PBMC cells treated or not treated with the antibodies are shown in FIG. 10. These results show that the antibody F4-1 is capable of reducing the titer of the virus by about log 2 with respect to untreated cells or cells treated with monoreactive anti-Tat antibody. Further, these results also show that the antibody F14-6, which does not inhibit HIV-1 when it is tested alone, caused a reduction in the infectious titer in synergy with the antibody J20-8 which alone had no inhibiting activity.

It is highly probable that the action of the antibody of the invention is exerted once the antibody has penetrated into the cells, as illustrated by the fact that pre-incubation of cells with the antibody can induce a strong inhibition of HIV-1 infectiousness. Further, preliminary experiments indicate that treatment with antibody does not modify virus-cell recognition via the CD4 molecule, which suggests a specific and intranuclear effect of the antibodies of the invention on HIV infectiousness and replication.

10. Inhibition of HIV

This Example again illustrates the properties of the compositions of the invention, in particular polypeptides, on a further HIV isolate.

Human peripheral blood mononuclear cells (PBMC) were activated in the presence of phytohemagglutinin for 3 days, then re-suspended in a culture medium in the presence of interleukin-2. The cells were then pre-incubated for 4 hours at 37° C. with 25 μg or 50 μg per $2\times10^6$ of the following polypeptides or antibodies:

P3 peptide: this peptide corresponds to the peptide pF4.1 in SEQ ID no 7.

P3PL peptide: this peptide corresponds to peptide K19-pF4.1of SEQ ID no 10.

F4-1 antibody.

By way of comparison, the cells were also incubated in the presence of AZT.

After incubation, the cells were washed in fresh culture medium then infected with 0.5 ml of a viral HIV-1 BX 08 strain dilution, ($10^{-3}$ to $10^{-5}$ or $10^{-1}$ to $10^{-4}$ depending on the experiment) into a stock of $2\times10^6$ cells for 1 hour at 37° C. The cells were then washed 3 times in fresh medium and re-suspended in medium containing the above peptides or antibodies (12.5 μg or 25 μg) and distributed over 48 well plates in an amount of 4 wells per dose of virus and peptide/antibody. The culture medium, containing peptides/antibodies, was changed every 3 or 4 days. Then viral production (consequence of infection and replication) was estimated by assaying the p24 antigen in the culture supernatants, under the conditions described in the Method and Apparatus section.

Figure 11A:
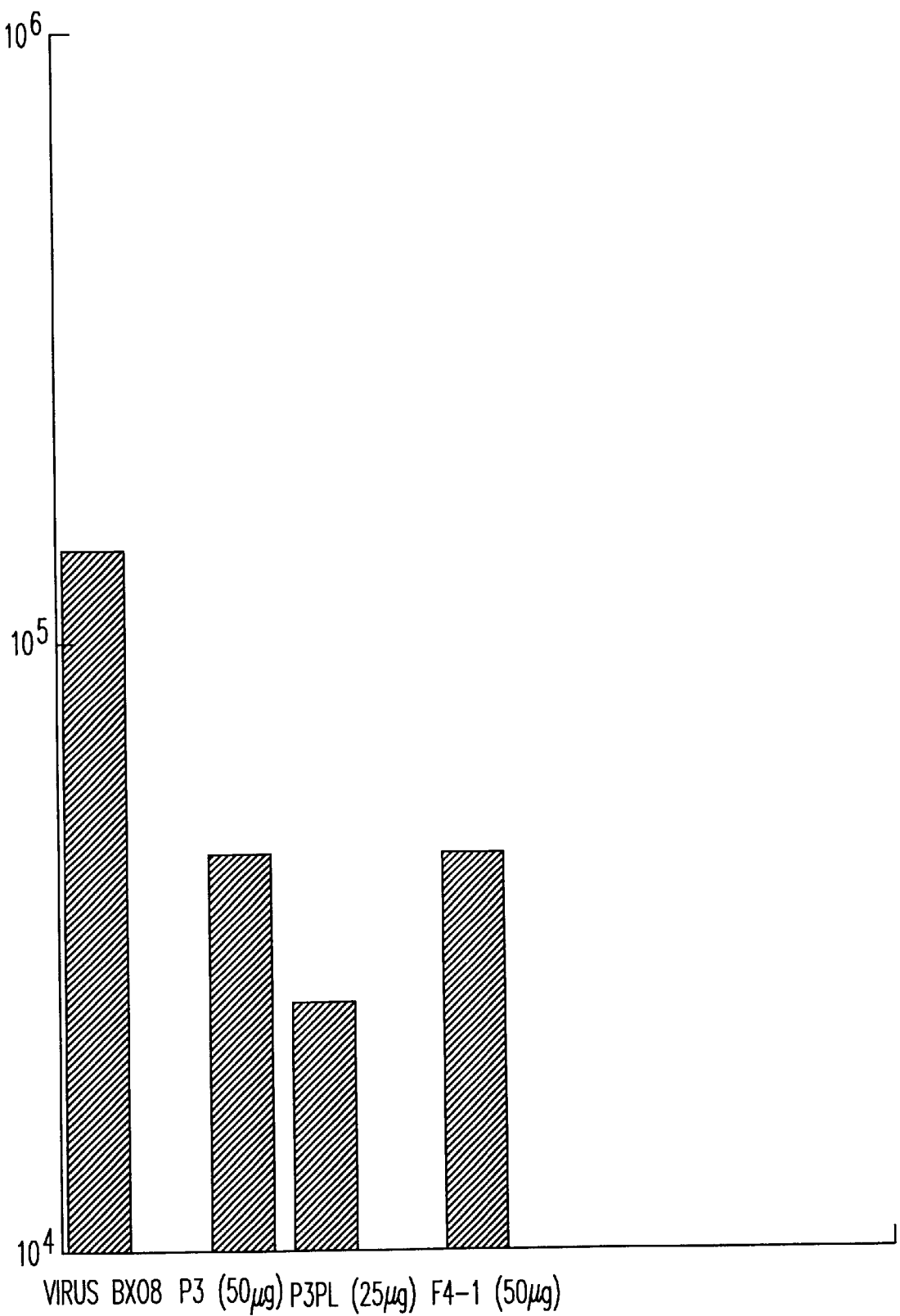
FIG. 11: Infectious titers and determination of the p24 antigen of HIV1 produced in human PBMC culture medium treated with different preparations of polypeptides or antibody and infected with strain HIV1 BX 08.
Figure 11B:
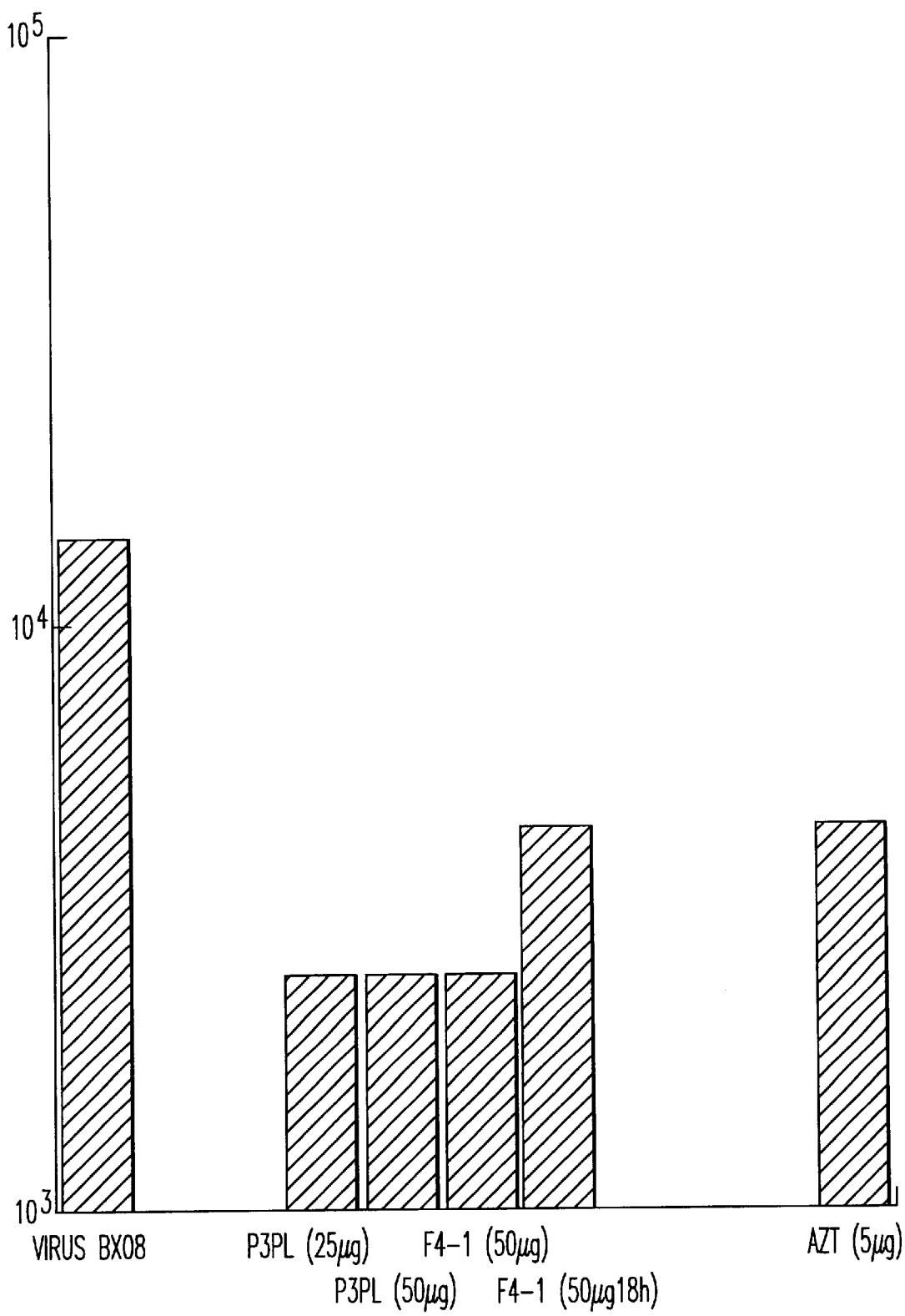
Figure 11C:
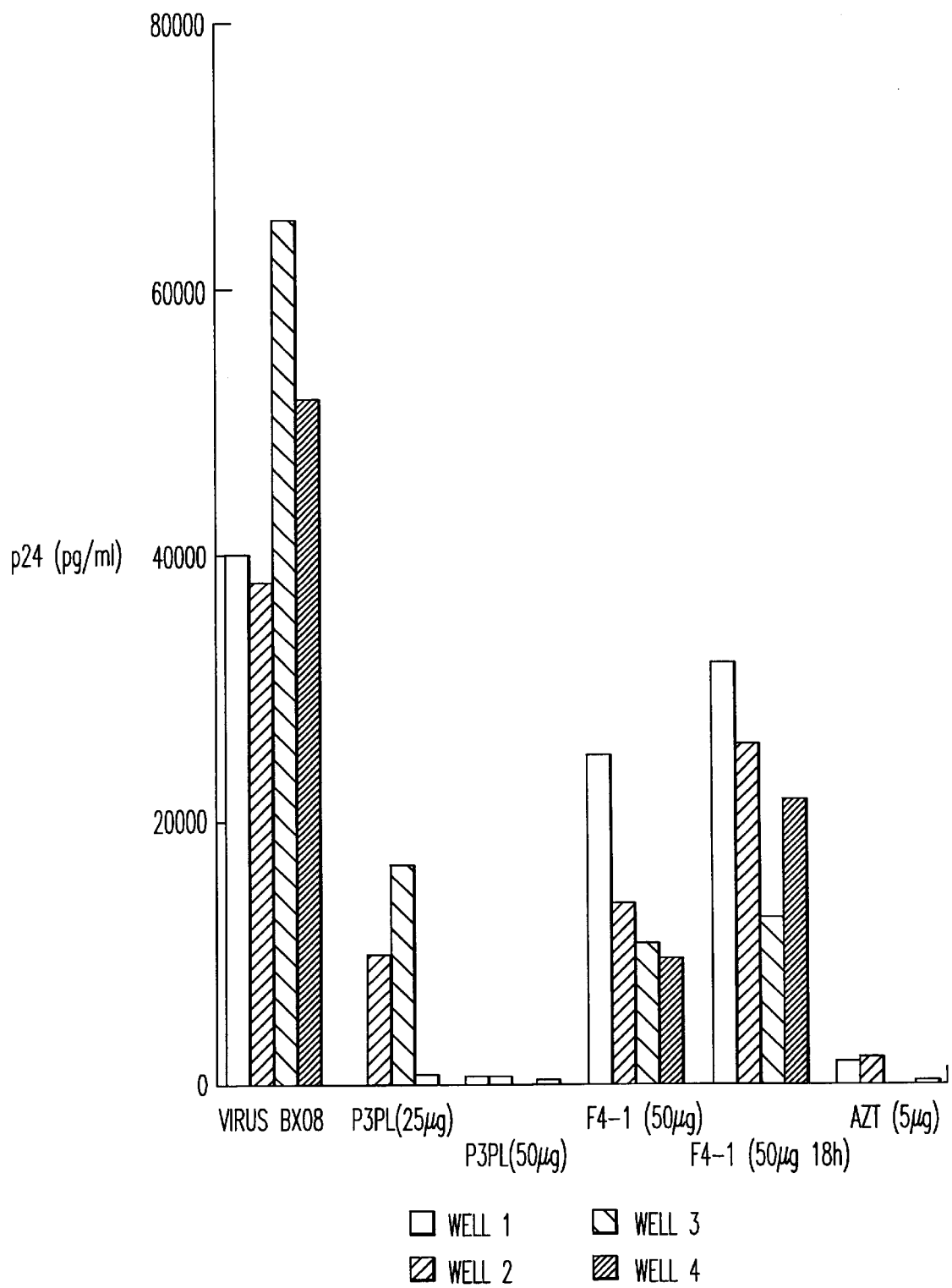

The results of several series of experiments are shown in FIGS. 11A, 11B and 11C.

As for Example 9, these results illustrate the capacity of polyreactive anti-DNA antibody or polypeptides to reduce replication of HIV in target cells, at different doses.

11. Inhibition of Polio Virus

This example illustrates the antiviral properties of the products of the invention for polio virus.

In order to test the inhibiting power of the peptides K19pF4.1, K19pJ20.8, K19pF14.6 on polio virus replication, two strains of type 1 polio virus (PV1) were used: the PVA/Mahoney wild type strain and the PV1/Sabin attenuated strain. The inhibiting power of the peptides was evaluated by measuring the titer reduction factor of a viral suspension of polio virus in the presence of peptide. The viral suspension titer was determined in terms of the cytopathogenic 50 dose (CPD50) per ml on Hep-2c human epithelial cells using a dilution limit microtechnique (Melnick et al., 1979, Melnick, J. L., Wenner, H. A., and Philips, C. A., (1979). Enteroviruses, in "Diagnostic procedure for viral, rickettsial and chlamydial infections" (E. H. Lennette and N. J. Schmidt, Eds), pp. 471–534, American Public Health Association, Washington D.C.). The titer reduction factor thus corresponds to the ratio between the titer for the viral suspension in the absence of peptide and that in the presence of the test peptide.

Apparatus

Peptides

Peptides derived from anti-DNA monoclonal antibody:
K19pF4.1 (SEQ ID no 10);
K19pFJ20.8
$(K)_{19}$-V-A-Y-I-S-R-G-G-G-I-F-Y-Y-Q-D-S-I-K-G-R-F-T-R-E-K-Y-G-K-R-G-M-D-Y (SEQ ID NO:36);
K19PF14.6
$(K)_{19}$-A-I-S-R-G-G-G-Y-S-Y-Y-L-D-T-V-K-R-T-A-R-A-T-W-D-W-F-A-Y. (SEQ ID NO:24)

Peptide used as negative control: K19PT corresponding to an ovalbumin peptide with 20 amino acids carrying 19 N-terminal lysines.

Virus

Wild type polio virus type 1 strain: PV1/Mahoney;
Attenuated polio virus type 1 strain: PV1/Sabin.

Cells

Hep-2c human epithelial cells originating from an epidermoid carcinoma of the larynx.

Protocol

On day 1, the cells were placed in culture. To this end, a suspension of $2.5 \times 10^5$ cells/ml in a MEM medium, 10% foetal calf serum (FCS), 0.5% gentamycin was prepared, and 5 plates of 96 wells were seeded with 200 μl/well (i.e., $5 \times 10^4$ cells/well). The cells were incubated at 37° C. in the presence of 5% $CO_2$.

On day 0, the cells were pre-incubated with the peptides for 2 hours. To this end, the peptides indicated above were diluted to 50 μg/ml in MEM medium, 10% FCS, 0.5% gentamycin. The wells were emptied by aspiration, then 100 μl/well of medium+peptide (one plate per peptide) was added. As a control a plate was prepared with 100 μl/well or medium with no peptide for titrating viral suspension in the absence of peptide. The mixture was incubated for 2 hours at 37° C. in the presence of 5% of $CO_2$.

In parallel, dilutions of viral suspensions were prepared, of 10 in 10 up to $10^{-4}$, then dilutions of 4 in 4 up to $10^{-8.8}$ in MEM medium, with no FCS, 0.5% gentamycin (50 μl/well and 4 wells/dilution).

For use during infection, the peptides were diluted in MEM medium, 3% FCS, 0.5% gentamycin so as to obtain a final concentration of 25 μg/ml of peptide (knowing that for the test, 150 μl of medium containing the peptide was added to 50 μl of viral dilution).

The infection step was carried out by emptying the wells (by aspiration) then adding the following elements:
150 μl/well of diluted peptide or medium for the untreated plate;
50 μl/well of $10^{-5.8}$ to $10^{8.8}$ viral dilutions, 4 wells/dilution.

Incubation was at 37° C. for 5 days in the presence of 5% Of $CO_2$.

5 days after infection, the CPD50/ml titers were determined as described above.

The results obtained are shown in the Table below and in FIG. 12. These results show the capacity of the polypeptides of the invention, used alone, to inhibit replication of different strains of polio virus.

TABLE

| VIRUS | PEPTIDE | LOG (TITER/ML) | TITER REDUCTION FACTOR |
|---|---|---|---|
| PV1/Mahoney | none | 9.65 | |
| | K19pF4-1 | 8.75 | 8 |
| | K19pJ20-8 | 8.9 | 6 |
| | K19PF14-6 | 9.05 | 4 |
| | K19PT | 8.75 | 8 |
| PV1/Sabin | none | 9.5 | |
| | K19pF4-1 | 8 | 32 |
| | K19pJ20-8 | 8.6 | 8 |
| | K19PF14-6 | 8.6 | 8 |
| | K19PT | 8.6 | 8 |

In particul ar, these results show that the K19-pe4.1 peptide has a very pronounced inhibiting effect on type 1 polio virus replication, by a factor of more than 30. This experiment illustrates the multiple applications of the present invention for inhibiting different types of virus.

12. Inhibition of Cytomegalovirus (CMV) Replication

This example illustrates the antiviral properties of compounds of the invention on cytomegalovirus.

Apparatus

Cells:

Human diploid fibroblasts and primary human astrocytomas (U373MG) were used. They were cultivated in a Dulbecco medium with a supplemental 2 mM of glutamine and 10% of foetal calf serum.

Peptides:

The compound used was the K19pF4-1 peptide derivative.

Virus:

The CMV Ad169 strain (ATCC VR538) was used. CMV titration was carried out by counting the plaques formed under carboxymethyl cellulose (0.6%).

Procedure:

The cells were treated with trypsine, washed, distributed in the wells of culture plates in an amount of $10^5$ per well and cultivated for 6 to 24 hours. The polypeptides, in sterile solution, were added to the cultures in a final concentration of 25 to 50 μg/ml. The cells were infected in an infection multiplicity of 1 pfu/cell.

Three operating procedures were followed:
a) the polypeptides were added 4 hours before viral infection;
b) the polypeptides were added at the same time as the virus;
c) the polypeptides were added after absorption of the virus on the cells (2 hours at 37° C.).

The antiviral effect was evaluated:
1) visually by observing the morphological appearance of the cells under an optical microscope;
2) by titrating the viral multiplication by counting the plaques formed 5 days after infection; and
3) by Western blot analysis of the appearance of very early, early and late viral infection proteins.

Results

The results obtained showed that:

1) the cells treated with K19-pF4-1, before or at the same time as the viral infection, displayed no morphological modifications (cytopathogenic effects: CPE). In contrast, the CPE of cells treated with K19-pF4.1 at the end of viral adsorption was large 24 to 48 hours after infection. Treated or untreated cells after viral adsorption with K19-pF4.1 or free polylysine of 19 residues (K19) demonstrated large CPEs.

2) Virus replication was inhibited by 99.5% in cells treated with K19-pF4.1 before, and at the same time, as viral infection (see Table below).

Figure 13A:
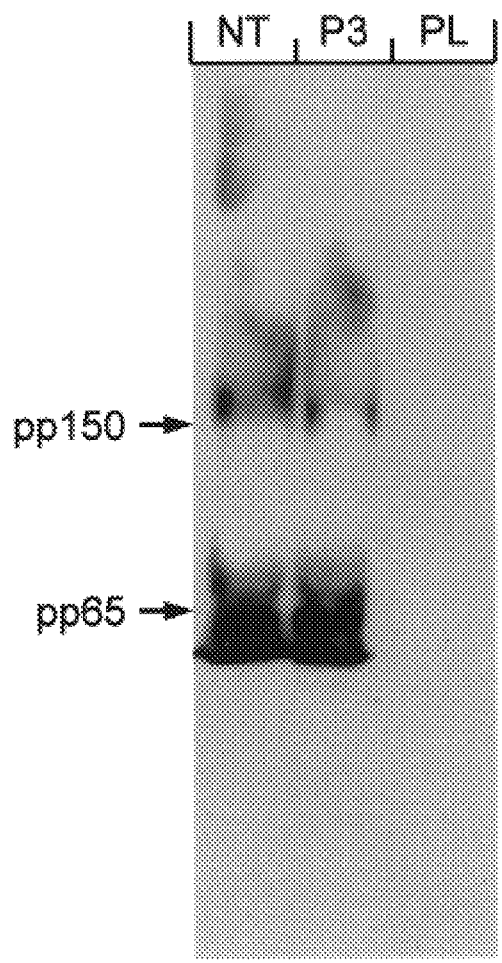
Figure 13B:
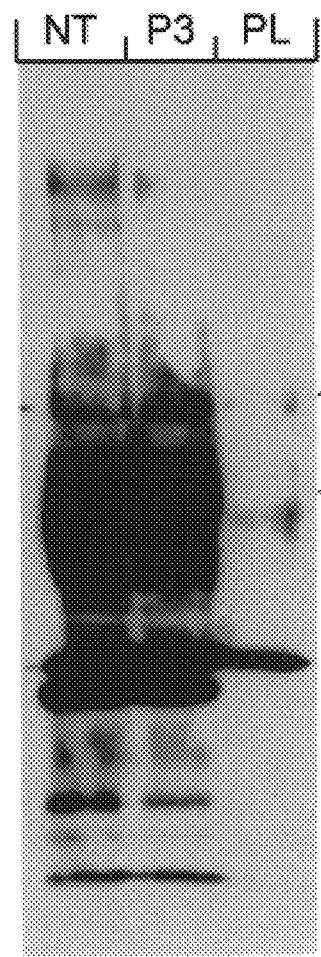
Figure 13C:
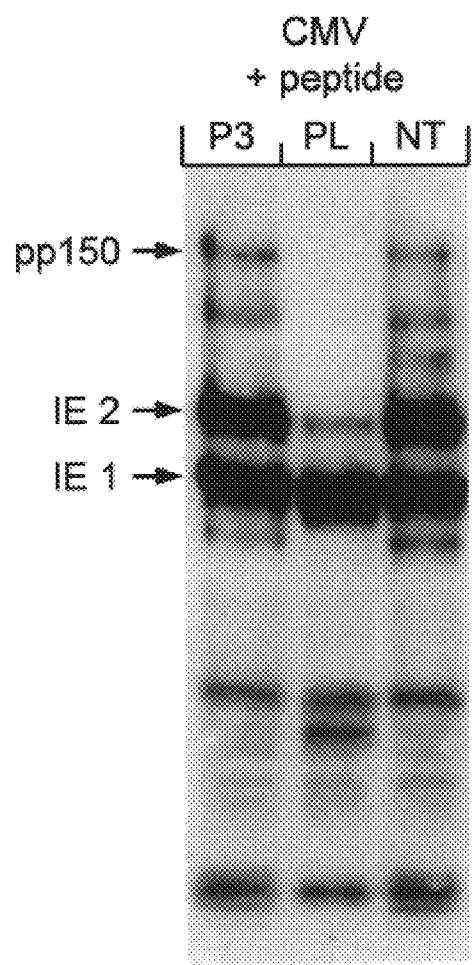
Figure 13D:
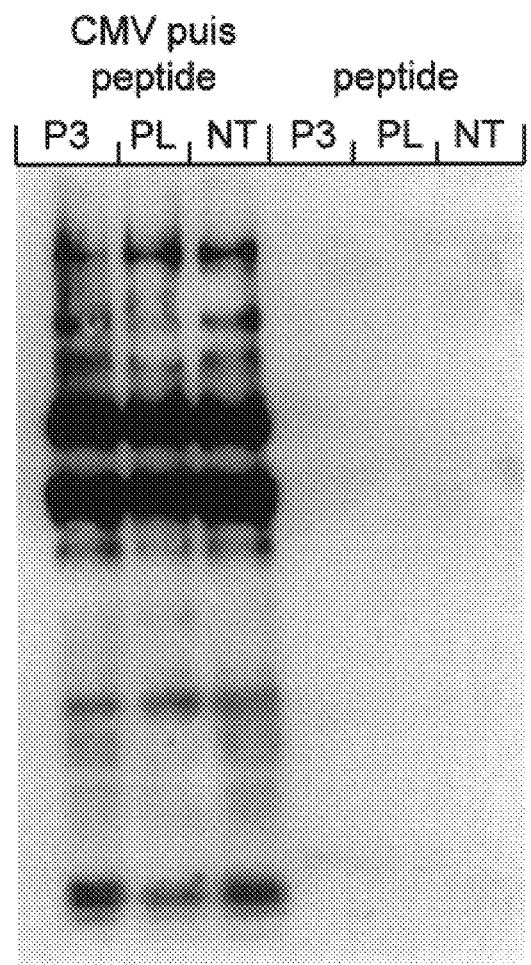

3) In cells treated with K19-F4.1 before viral infection, the appearance of neither early proteins nor late proteins of the CMV was noted (FIGS. 13a and 13b). In cells treated with K19-pF4.1 at the same time as viral infection, no appearance of late proteins was noted, but the appearance, albeit reduced in quantity, of very early proteins was noted (FIG. 13c) K19-pF4.1 had no action if it was added to cells after viral adsorption (FIG. 13d).

In conclusion, the results show that the K19-pF4.1 polypeptide significantly inhibits CMV replication when the cells are treated with this polypeptide before viral infection. When it is added to cells at the same time as CMV, the peptide is also effective, but can be to a lesser extent (appearance of early antigens).

TABLE

NUMBER OF PLAQUES FORMED

| | | | | Mean | SD | % reduct'n |
|---|---|---|---|---|---|---|
| Day 1 | | | | | | |
| No rx | 50 | 50 | 0 | 33.333 | 28.9 | |
| K19-pF4.1 | 100 | 125 | 75 | 100.0 | 25.0 | |
| Day 4 | | | | | | |
| No rx | 18000 | 50750 | 31500 | 33416.7 | 16458.9 | |
| K19-pF4.1 | 0 | 250 | 250 | 166.7 | 144.3 | 99.5 |

CMV titrations 5 days after infection with 25 μg/ml of cells pretreated with K19-pF4.1 or with no treatment (no Rx).

13. Inhibition of Herpes Virus

This example illustrates the antiviral properties of the compounds of the invention on the herpes simplex virus.

The antiviral activity was determined by measuring the cytopathogenic effect (CPE) induced by a HSV-1 TK$^+$ virus (i.e., expressing thymidine kinase) and by a HSV-1 TK$^-$ virus (i.e., not expressing thymidine kinase, and thus insensitive to AZT).

The following peptides and antibodies were used: K19, K19-pF4.1, K19-pJ20.8, K19-pF14.6 and F14.6.

Acyclovir® was used as the reference anti HSV-1 TK$^+$ compound (2 mg, MW 225, Wellcome). The Acyclovir was dissolved n 2 ml of DMEM 1×medium supplemented with antibiotics, then 50 μl of 1N NaOH was added. The volume was adjusted to 4.44 ml with DMEM 1×medium, AB, and the pH was adjusted to 7–7.4 using 1N HCl. The neutralised solutions were sterilised on 0.45 μm filters, then preserved in aliquots at −20° C. The solution ($10^{-2}$ M) was diluted to 1/10 to 1/10$^4$ just before use (from $10^{-3}$ M) and added in an amount of 50 μl 1 hour after infection.

The viral stocks (HSV-1 TK$^+$, seventh passage over Vero cells, and HSV-1 TK$^-$, fourth passage) were diluted to 1/100 in culture medium prior to distribution on plates (50 μl/well).

The CPE inhibition test is a semi-quantitative test which measures the % survival of the cells. The following protocol was followed: Vero cells were trypsinised (trypsin-versene, Eurobio), distributed in flat bottomed 96-well plates (Falcon) in an amount of 2×10$^4$ cells per well, in 50 μl of DMEM medium (Bioproducts) supplemented with antibiotics, L-glutamine and 5% FCS (Eurobio), then incubated for 24 hours. The peptide/antibodies, sterilised on a 0.22 μM filter, were added in an amount of 50 to 400 μg/ml (i.e., 20 to 2.5 μg/well) using the following schedule:

H-24: cells into culture;

H-0: infection;

H-2, H-1, H0, H+1: add peptides;

H+48: CPE test.

48 hours after infection, the medium was removed and the wells were washed 3 times with 200 μl of sterile PBS buffer containing Ca$^{2+}$ and Mg$^{2+}$, so as to eliminate dead cells. Neutral Red (RAL, 0.3%) was added (100 μl/well) and the cells were incubated for 2 more hours. The cells were then washed 3 times as described above to eliminate colorant which had not been incorporated into the cells. The cells were then exploded by adding 100 μl of 1% SDS in distilled water. After 1 hour at 4° C. to completely leach out the Neutral Red, the crystals were dissolved with a pipette. Air bubbles were destroyed by a current of hot air (hair dryer) and the plates were read, using a microplate reader at 570 nm using a 630 nm reference filter. The optical density blank was air.

The following controls were used:

Reference cells: non infected and non treated, incubated with Neutral Red;

Reference virus: infected cells with different dilutions of a factor of 2 of virus, from 100% CPE (dilution 1/1) to 12.5% CPE (1/8 dilution);

Antiviral reference: cells treated with acyclovir and infected; and

Toxicity reference: non infected cells, treated with different peptides/antibodies.

Viral activity was determined as follows:

AI=100×(OD cell+virus+peptide)−OD(ref virus 100% CPE OD ref cells−OD ref virus 100% CPE.

The results obtained are shown in the following tables. The results clearly show an inhibition of the CPE effect induced by a HSV-1 TK$^+$ and TK$^-$ virus. The observed effect is particularly pronounced for the K19-pJ20.8 peptide, which is very active against the two viral strains, in particular with incubation prior to or simultaneously with viral infection.

The results presented below thus demonstrate the important antiviral properties of the antibodies/peptides of the invention, used alone or in combination, on different types of virus such as HIV, polio virus, CMV and HSV-1. These results illustrate the applications of the products of the invention to minimise the effects of viral infection in vitro, ex vivo or in vivo.

Control tables

REFERENCE VIRUS

| Dilution | HSV1 TK+ | HSV1 TK− |
|---|---|---|
| 0/0 (control cell) | 1.292 ± 0.146 | 1.292 ± 0.146 |
| 1/1 | 0.163 ± 0.060 | 0.297 ± 0.068 |
| 1/2 | 0.206 ± 0.062 | 0.246 ± 0.072 |
| 1/4 | 0.217 ± 0.041 | 0.252 ± 0.058 |
| 1/8 | 0.227 ± 0.039 | 0.289 ± 0.029 |

ANTIVIRAL REFERENCE (ACYCLOVIR ®)

| Conc. (M)/HSV | HSV1 TK+ | HSV1 TK− |
|---|---|---|
| $10^{-3}/0$ | 0.909 ± 0.016 | 0.789 ± 0.160 |
| $10^{-4}/0$ | 1.027 ± 0.042 | 0.834 ± 0.086 |
| $10^{-5}/0$ | 0.975 ± 0.093 | 0.869 ± 0.053 |
| $10^{-6}/0$ | 0.960 ± 0.025 | 0.816 ± 0.001 |
| $10^{-3}$/HSV | 0.626 ± 0.050 62% | 0.289 ± 0.055 0% |
| $10^{-4}$/HSV | 0.587 ± 0.149 49% | 0.173 ± 0.001 0% |
| $10^{-5}$/HSV | 0.223 ± 0.017 7% | 0.169 ± 0.019 0% |
| $10^{-6}$/HSV | 0.235 ± 0.032 9% | 0.239 ± 0.111 0% |

Test tables

HSV1 TK+ H-2

| Peptide μ/well | 20 | 10 | 5 |
|---|---|---|---|
| K19 | 0 | 0 | 0 |
| K19pF4-1 | 7 | 2 | 1 |
| K19PJ20-8 | 78 | 44 | 1 |
| K19pF14-6 | TOX(*) | TOX | 1 |
| F14-6 | 0 | 0 | 0 |

(*)Toxic

HSV1 TK+ H-1

| Peptide μ/well | 20 | 10 | 5 |
|---|---|---|---|
| K19 | 9 | 6 | 8 |
| K19pF4-1 | 28 | 30 | 13 |
| K19PJ20-8 | 89 | 74 | 27 |
| K19pF14-6 | TOX | TOX | 8 |
| F14-6 | 0 | 0 | 0 |

HSV1 TK+ H0

| Peptide μ/well | 20 | 10 | 5 |
|---|---|---|---|
| K19 | 32 | 14 | 13 |
| K19pF4-1 | 28 | 30 | 13 |
| K19PJ20-8 | 86 | 71 | 37 |
| K19pF14-6 | TOX | TOX | 69 |
| F14-6 | 0 | 0 | 0 |

HSV1 TK+ H + 1

| Peptide μ/well | 20 | 10 | 5 |
|---|---|---|---|
| K19 | 0 | 0 | 6 |
| K19pF4-1 | 10 | 12 | 10 |
| K19PJ20-8 | 0 | 1 | 0 |
| K19pF14-6 | TOX | TOX | 37 |
| F14-6 | 0 | 0 | 0 |

HSV1 TK− H-2

| Peptide μ/well | 20 | 10 | 5 |
|---|---|---|---|
| K19 | 0 | 26 | 27 |
| K19pF4-1 | 25 | 5 | 21 |
| K19PJ20-8 | 0 | 46 | 55 |
| K19pF14-6 | TOX | TOX | 100 |
| F14-6 | 0 | 21 | 24 |

HSV1 TK− H-1

| Peptide μ/well | 20 | 10 | 5 |
|---|---|---|---|
| K19 | 34 | 4 | 0 |
| K19pF4-1 | 47 | 7 | 25 |
| K19PJ20-8 | 100 | 49 | 29 |
| K19pF14-6 | TOX | TOX | 72 |
| F14-6 | 0 | 0 | 0 |

HSV1 TK− H0

| Peptide μ/well | 20 | 10 | 5 |
|---|---|---|---|
| K19 | 40 | 2 | 0 |
| K19pF4-1 | 42 | 25 | 15 |
| K19PJ20-8 | 86 | 56 | 38 |
| K19pF14-6 | TOX | 92 | 81 |
| F14-6 | 0 | 0 | 0 |

HSV1 TK− H + 1

| Peptide μ/well | 20 | 10 | 5 |
|---|---|---|---|
| K19 | 2 | 0 | 0 |
| K19pF4-1 | 1 | 13 | 1 |
| K19PJ20-8 | 11 | 3 | 1 |
| KT9pF14-6 | TOX | TOX | 26 |
| F14-6 | 0 | 0 | 0 |

This set of results clearly demonstrates that the polypeptides of the invention, comprising an antibody region, preferably comprising all or a portion of a CDR3, are capable (i) of effectively penetrating into cells; (ii) of transporting substances thereto, in particular large size substances; (iii), of acting as an adjuvant in vivo by stimulating the immune response against a given antigen; and (iv) of exerting an antiviral activity. Further, the polypeptides of the invention even appear to be able to transport substances to the cell nuclei, which is of obvious interest when the substances are nucleic acids or molecules acting on nucleic acids. Further, the polypeptides of the invention appear to use a cell penetration mechanism which is different from the majority of vectors used up to the present time. In particular, the polypeptides of the invention appear to escape the lysosomes, which constitutes an additional advantage in that in general, substantial degradation occurs in those cellular compartments.

What is claimed is:

1. An isolated polypeptide, consisting of a single chain of amino acids, wherein said single chain of amino acids comprises one or more penetrating fragments from one or more penetrating antibodies, and wherein said isolated polypeptide penetrates into a cell.

2. The isolated polypeptide of claim 1, wherein said single chain of amino acids comprises all or a portion of an antibody hypervariable region.

3. The isolated polypeptide of claim 1, wherein said single chain of amino acids comprises one or more heavy chain antibody fragments.

4. The isolated polypeptide of claim 3, herein said heavy chain antibody fragment comprises all or a portion of a CDR3 region of said heavy chain antibody.

5. The isolated polypeptide of claim 3, wherein said heavy chain antibody fragments comprises all or a portion of a CDR2 region of said heavy chain antibody.

6. The isolated polypeptide of claim 3, wherein said fragment of a heavy antibody chain comprises all or a portion of the CDR3 region and all or a portion of the CDR2 region of said heavy chain antibody.

7. The isolated polypeptide of claim 6, which consists essentially of a fusion between the CDR3 region and a CDR2 region of said heavy chain antibody.

8. The isolated polypeptide of claim 1, which comprises at most 100 amino acids.

9. The isolated polypeptide of claim 8, which comprises from 3 to 60 amino acids.

10. The isolated polypeptide of claim 8, which comprises from 3 to 30 amino acids.

11. The isolated polypeptide of claim 1, wherein said penetrating antibody is a polyreactive antibody.

12. The isolated polypeptide of claim 1, wherein said penetrating antibody is an anti-DNA antibody.

13. The isolated polypeptide of claim 1, which comprises a sequence selected from the group consisting of SEQ ID NO:1, amino acids 2–17 of SEQ ID NO:1, amino acids 3–17 of SEQ ID NO:1, amino acids 4–17 of SEQ ID NO:1, and a functional homologue thereof.

14. The isolated polypeptide of claim 1, wherein said single chain of amino acids comprises a basic amino acid region.

15. The isolated polypeptide of claim 14, wherein said basic amino acid is lysine.

16. The isolated polypeptide of claim 1, wherein said single chain of amino acids is obtained by screening a peptide library for a cell penetration activity.

17. The isolated polypeptide of claim 1, wherein said polypeptide reacts in vitro with one or more macromolecules selected from the group consisting of anionic macromolecules, double-stranded RNA, single-stranded RNA, DNA, cationic macromolecules and histones.

18. The isolated polypeptide of claim 1, which reacts in vitro with heparin and heparin sulphate.

19. An isolated polypeptide, consisting of a polylysine region and a single chain of amino acids from a penetrating polyreactive antibody, wherein the isolated polypeptide penetrates into a cell.

20. The isolated polypeptide claim 19, wherein said polypeptide reacts in vitro with one or more macromolecules selected the group consisting of anionic macromolecules, double-stranded RNA, single-stranded RNA, DNA, cationic macromolecules and histones.

21. The isolated polypeptide of claim 19, which reacts in vitro with heparin and heparin sulphate.

* * * * *

SEQUENCE LISTING

<160> NUMBER OF SEQ ID NOS: 36

<210> SEQ ID NO 1
<211> LENGTH: 17
<212> TYPE: PRT
<213> ORGANISM: Artificial Sequence

```
<220> FEATURE:
<223> OTHER INFORMATION: SYNTHETIC PEPTIDE

<400> SEQUENCE: 1

Thr Arg Gln Lys Tyr Asn Lys Arg Ala Met Asp Tyr Trp Gly Gln Gly
1               5                   10                  15

Thr

<210> SEQ ID NO 2
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 2

Thr Arg Gln Lys Tyr Gly Lys Arg Gly Met Asp Tyr Trp Gly Gln Gly
1               5                   10                  15

Thr

<210> SEQ ID NO 3
<211> LENGTH: 18
<212> TYPE: PRT
<213> ORGANISM: Artificial Sequence
<220> FEATURE:
<223> OTHER INFORMATION: SYNTHETIC PEPTIDE

<400> SEQUENCE: 3

Thr Arg Gln Ala Arg Ala Thr Trp Asp Trp Phe Ala Tyr Trp Gly Gln
1               5                   10                  15

Gly Thr

<210> SEQ ID NO 4
<211> LENGTH: 22
<212> TYPE: PRT
<213> ORGANISM: Artificial Sequence
<220> FEATURE:
<223> OTHER INFORMATION: SYNTHETIC PEPTIDE

<400> SEQUENCE: 4

Val Ala Tyr Ile Ser Arg Gly Gly Val Ser Thr Tyr Tyr Ser Asp Thr
1               5                   10                  15

Val Lys Gly Arg Phe Thr
            20

<210> SEQ ID NO 5
<211> LENGTH: 21
<212> TYPE: PRT
<213> ORGANISM: Artificial Sequence
<220> FEATURE:
<223> OTHER INFORMATION: SYNTHETIC PEPTIDE

<400> SEQUENCE: 5

Val Ala Tyr Ile Ser Arg Gly Gly Gly Ile Phe Tyr Tyr Glu Asp Ser
1               5                   10                  15

Ile Lys Gly Arg Phe
            20

<210> SEQ ID NO 6
<211> LENGTH: 23
<212> TYPE: PRT
<213> ORGANISM: Artificial Sequence
<220> FEATURE:
<223> OTHER INFORMATION: SYNTHETIC PEPTIDE
```

<400> SEQUENCE: 6

Val Ala Ala Ile Ser Arg Gly Gly Tyr Ser Tyr Tyr Leu Asp Ser
1               5                   10                  15

Val Lys Gly Arg Phe Thr Ile
            20

<210> SEQ ID NO 7
<211> LENGTH: 30
<212> TYPE: PRT
<213> ORGANISM: Artificial Sequence
<220> FEATURE:
<223> OTHER INFORMATION: SYNTHETIC PEPTIDE

<400> SEQUENCE: 7

Val Ala Tyr Ile Ser Arg Gly Gly Val Ser Thr Tyr Tyr Ser Asp Thr
1               5                   10                  15

Val Lys Gly Arg Phe Thr Arg Gln Lys Tyr Asn Lys Arg Ala
            20                  25                  30

<210> SEQ ID NO 8
<211> LENGTH: 12
<212> TYPE: PRT
<213> ORGANISM: Artificial Sequence
<220> FEATURE:
<223> OTHER INFORMATION: SYNTHETIC PEPTIDE

<400> SEQUENCE: 8

Ala Arg Gln Lys Tyr Asn Lys Arg Ala Met Asp Tyr
1               5                   10

<210> SEQ ID NO 9
<211> LENGTH: 31
<212> TYPE: PRT
<213> ORGANISM: Artificial Sequence
<220> FEATURE:
<223> OTHER INFORMATION: SYNTHETIC PEPTIDE

<400> SEQUENCE: 9

Cys Val Ala Tyr Ile Ser Arg Gly Gly Val Ser Thr Tyr Tyr Ser Asp
1               5                   10                  15

Thr Val Lys Gly Arg Phe Thr Arg Gln Lys Tyr Asn Lys Arg Ala
                20                  25                  30

<210> SEQ ID NO 10
<211> LENGTH: 49
<212> TYPE: PRT
<213> ORGANISM: Artificial Sequence
<220> FEATURE:
<223> OTHER INFORMATION: SYNTHETIC PEPTIDE

<400> SEQUENCE: 10

Lys Lys Lys Lys Lys Lys Lys Lys Lys Lys Lys Lys Lys Lys Lys Lys
1               5                   10                  15

Lys Lys Lys Val Ala Tyr Ile Ser Arg Gly Gly Val Ser Thr Tyr Tyr
                20                  25                  30

Ser Asp Thr Val Lys Gly Arg Phe Thr Arg Gln Lys Tyr Asn Lys Arg
            35                  40                  45

Ala

<210> SEQ ID NO 11
<211> LENGTH: 26
<212> TYPE: DNA

```
<213> ORGANISM: Artificial Sequence
<220> FEATURE:
<223> OTHER INFORMATION: SYNTHETIC DNA

<400> SEQUENCE: 11
gttctgacta gtgggcactc tgggct                                              26

<210> SEQ ID NO 12
<211> LENGTH: 26
<212> TYPE: DNA
<213> ORGANISM: Artificial Sequence
<220> FEATURE:
<223> OTHER INFORMATION: SYNTHETIC DNA

<400> SEQUENCE: 12
gaggttcagc tcgagcagtc tggggc                                              26

<210> SEQ ID NO 13
<211> LENGTH: 26
<212> TYPE: DNA
<213> ORGANISM: Artificial Sequence
<220> FEATURE:
<223> OTHER INFORMATION: SYNTHETIC DNA

<400> SEQUENCE: 13
gaggtgaagc tcgaggaatc tggagg                                              26

<210> SEQ ID NO 14
<211> LENGTH: 25
<212> TYPE: DNA
<213> ORGANISM: Artificial Sequence
<220> FEATURE:
<223> OTHER INFORMATION: SYNTHETIC DNA

<400> SEQUENCE: 14
gaagtgcagc tcgaggagtc tgggg                                               25

<210> SEQ ID NO 15
<211> LENGTH: 26
<212> TYPE: DNA
<213> ORGANISM: Artificial Sequence
<220> FEATURE:
<223> OTHER INFORMATION: SYNTHETIC DNA

<400> SEQUENCE: 15
gaggttcagc tcgagcagtc tggagc                                              26

<210> SEQ ID NO 16
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 16

Thr Arg Gln Lys Tyr Asn Lys Arg Ala Met Asp Tyr Trp Gly Gln Gly
1               5                   10                  15

Thr

<210> SEQ ID NO 17
<211> LENGTH: 18
<212> TYPE: PRT
<213> ORGANISM: Artificial Sequence
<220> FEATURE:
<223> OTHER INFORMATION: SYNTHETIC PEPTIDE
```

```
<400> SEQUENCE: 17

Thr Arg Gln Lys Tyr Asn Lys Lys Arg Gly Met Asp Tyr Trp Gly Gln
1               5                   10                  15

Gly Thr

<210> SEQ ID NO 18
<211> LENGTH: 18
<212> TYPE: PRT
<213> ORGANISM: Artificial Sequence
<220> FEATURE:
<223> OTHER INFORMATION: SYNTHETIC PEPTIDE

<400> SEQUENCE: 18

Thr Arg Gly Ala Arg Ala Thr Trp Asp Trp Phe Ala Tyr Trp Gly Gln
1               5                   10                  15

Gly Thr

<210> SEQ ID NO 19
<211> LENGTH: 21
<212> TYPE: PRT
<213> ORGANISM: Artificial Sequence
<220> FEATURE:
<223> OTHER INFORMATION: SYNTHETIC PEPTIDE

<400> SEQUENCE: 19

Val Ala Tyr Ile Ser Arg Gly Gly Val Ser Thr Tyr Tyr Ser Asp Thr
1               5                   10                  15

Val Lys Gly Arg Phe
            20

<210> SEQ ID NO 20
<211> LENGTH: 22
<212> TYPE: PRT
<213> ORGANISM: Artificial Sequence
<220> FEATURE:
<223> OTHER INFORMATION: SYNTHETIC PEPTIDE

<400> SEQUENCE: 20

Val Ala Tyr Ile Ser Arg Gly Gly Val Ser Thr Tyr Tyr Ser Asp Thr
1               5                   10                  15

Val Lys Gly Arg Phe Thr
            20

<210> SEQ ID NO 21
<211> LENGTH: 20
<212> TYPE: PRT
<213> ORGANISM: Artificial Sequence
<220> FEATURE:
<223> OTHER INFORMATION: SYNTHETIC PEPTIDE

<400> SEQUENCE: 21

Val Ala Tyr Ile Ser Arg Gly Gly Ile Phe Tyr Tyr Gln Asp Ser Ile
1               5                   10                  15

Lys Gly Arg Phe
            20

<210> SEQ ID NO 22
<211> LENGTH: 23
<212> TYPE: PRT
<213> ORGANISM: Artificial Sequence
<220> FEATURE:
<223> OTHER INFORMATION: SYNTHETIC PEPTIDE

<400> SEQUENCE: 22
```

Val Ala Ala Ile Ser Arg Gly Gly Gly Tyr Ser Tyr Tyr Leu Asp Ser
1               5                   10                  15

Val Lys Gly Arg Phe Thr Ile
            20

<210> SEQ ID NO 23
<211> LENGTH: 33
<212> TYPE: PRT
<213> ORGANISM: Artificial Sequence
<220> FEATURE:
<223> OTHER INFORMATION: SYNTHETIC PEPTIDE

<400> SEQUENCE: 23

Val Ala Tyr Ile Ser Arg Gly Gly Val Ser Thr Tyr Tyr Ser Asp Thr
1               5                   10                  15

Val Lys Gly Arg Phe Thr Arg Gln Lys Tyr Asn Lys Arg Ala Val Ala
            20                  25                  30

Tyr

<210> SEQ ID NO 24
<211> LENGTH: 47
<212> TYPE: PRT
<213> ORGANISM: Artificial Sequence
<220> FEATURE:
<223> OTHER INFORMATION: SYNTHETIC PEPTIDE

<400> SEQUENCE: 24

Lys Lys Lys Lys Lys Lys Lys Lys Lys Lys Lys Lys Lys Lys Lys Lys
1               5                   10                  15

Lys Lys Lys Ala Ile Ser Arg Gly Gly Gly Tyr Ser Tyr Tyr Leu Asp
            20                  25                  30

Thr Val Lys Arg Thr Ala Arg Ala Thr Trp Asp Trp Phe Ala Tyr
        35                  40                  45

<210> SEQ ID NO 25
<211> LENGTH: 105
<212> TYPE: PRT
<213> ORGANISM: Artificial Sequence
<220> FEATURE:
<223> OTHER INFORMATION: SYNTHETIC PEPTIDE

<400> SEQUENCE: 25

Gly Gly Ser Leu Lys Leu Ser Cys Ala Ala Ser Gly Phe Thr Phe Ser
1               5                   10                  15

Ser Tyr Ala Met Ser Trp Val Arg Gln Thr Pro Ala Lys Arg Leu Glu
            20                  25                  30

Trp Val Ala Tyr Ile Ser Arg Gly Gly Ile Phe Tyr Tyr Gln Asp
        35                  40                  45

Ser Ile Lys Gly Arg Phe Thr Ile Ala Arg Asp Asn Ala Lys Asn Thr
    50                  55                  60

Leu Tyr Leu Gln Met Ser Ser Leu Arg Ser Glu Asp Thr Ala Met Tyr
65                  70                  75                  80

Tyr Cys Thr Arg Glu Lys Tyr Gly Lys Arg Gly Met Asp Tyr Trp Gly
                85                  90                  95

Gln Gly Thr Ser Val Thr Val Ser Ser
            100                 105

<210> SEQ ID NO 26
<211> LENGTH: 107
<212> TYPE: PRT

<213> ORGANISM: Artificial Sequence
<220> FEATURE:
<223> OTHER INFORMATION: SYNTHETIC PEPTIDE

<400> SEQUENCE: 26

Glu Thr Gly Gly Ser Leu Lys Leu Ser Cys Ala Ala Ser Gly Phe Thr
1               5                   10                  15

Phe Ser Ser Tyr Ala Met Ser Trp Val Arg Gln Thr Pro Ala Lys Arg
            20                  25                  30

Leu Glu Trp Val Ala Tyr Ile Ser Arg Gly Gly Val Ser Thr Tyr Tyr
        35                  40                  45

Ser Asp Thr Val Lys Gly Arg Phe Thr Ile Ser Arg Asp Asn Ala Lys
    50                  55                  60

Asn Thr Leu Ser Leu Gln Met Ser Ser Leu Arg Ser Glu Asp Thr Ala
65                  70                  75                  80

Met Tyr Tyr Cys Ala Arg Gln Lys Tyr Asn Lys Arg Ala Met Asp Tyr
                85                  90                  95

Trp Gly Gln Gly Thr Ser Val Thr Val Ser Ser
            100                 105

<210> SEQ ID NO 27
<211> LENGTH: 110
<212> TYPE: PRT
<213> ORGANISM: Artificial Sequence
<220> FEATURE:
<223> OTHER INFORMATION: SYNTHETIC PEPTIDE

<400> SEQUENCE: 27

Ala Leu Val Lys Pro Gly Gly Ser Leu Lys Leu Ser Cys Ala Ala Ser
1               5                   10                  15

Gly Phe Thr Phe Ser Asn Tyr Gly Met Ser Trp Val Arg Gln Thr Pro
            20                  25                  30

Glu Lys Arg Leu Glu Trp Val Ala Ala Ile Ser Arg Gly Gly Gly Tyr
        35                  40                  45

Ser Tyr Tyr Leu Asp Ser Val Lys Gly Arg Phe Thr Ile Ser Arg Asp
    50                  55                  60

Asn Ala Arg Asn Thr Leu Tyr Leu Gln Met Ser Ser Leu Arg Ser Glu
65                  70                  75                  80

Glu Thr Ala Met Tyr Tyr Cys Ala Arg Thr Ala Arg Ala Thr Trp Asp
                85                  90                  95

Trp Phe Ala Trp Gly Gln Gly Thr Leu Val Thr Val Ser Ala
            100                 105                 110

<210> SEQ ID NO 28
<211> LENGTH: 109
<212> TYPE: PRT
<213> ORGANISM: Artificial Sequence
<220> FEATURE:
<223> OTHER INFORMATION: SYNTHETIC PEPTIDE

<400> SEQUENCE: 28

Glu Leu Val Arg Gly Ala Ser Val Lys Val Ser Cys Thr Thr Ser Gly
1               5                   10                  15

Phe Thr Asn Ile Lys Asp Asp Tyr Ile His Trp Val Arg Gln Arg Pro
            20                  25                  30

Glu Gln Gly Leu Glu Trp Ile Gly Arg Ile Asp Pro Ala Asn Gly Lys
        35                  40                  45

Thr Lys Tyr Ala Pro Lys Phe Gln Asp Lys Ala Thr Ile Thr Ala Asp
    50                  55                  60

Thr Ser Ser Asn Thr Ala Tyr Leu Gln Leu Ser Ser Leu Thr Ser Glu
65                  70                  75                  80

Asp Thr Ala Val Tyr Tyr Cys Ala Arg Gly Leu Thr Arg Trp Tyr Phe
                85                  90                  95

Asp Val Trp Gly Ala Gly Thr Thr Val Thr Leu Ser Ala
            100                 105

<210> SEQ ID NO 29
<211> LENGTH: 109
<212> TYPE: PRT
<213> ORGANISM: Artificial Sequence
<220> FEATURE:
<223> OTHER INFORMATION: SYNTHETIC PEPTIDE

<400> SEQUENCE: 29

Gly Leu Val Lys Pro Gly Ala Ser Val Lys Val Ser Cys Asn Val Ser
1               5                   10                  15

Gly Tyr Ser Phe Thr Gly Tyr Phe Met Asn Trp Val Arg Gln Ser His
                20                  25                  30

Gly Lys Ser Leu Glu Trp Val Gly Arg Ile Asn Pro Leu Asn Gly Asp
            35                  40                  45

Thr Phe Tyr Asn Gln Lys Phe Lys Gly Lys Ala Thr Leu Thr Val Asp
        50                  55                  60

Lys Ser Ser Thr Leu Ala His Met Glu Leu Arg Leu Arg Lys Ser Glu
65                  70                  75                  80

Asn Ser Ala Val Tyr Tyr Cys Ala Arg Gly Leu Thr Arg Trp Tyr Phe
                85                  90                  95

Met Val Trp Gly Ala Gly Thr Thr Val Thr Leu Ser Ala
            100                 105

<210> SEQ ID NO 30
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 30

Tyr Ile Ser Arg Gly Gly Gly Ile Phe Tyr Tyr Gln Asp Ser Ile Lys
1               5                   10                  15

Gly

<210> SEQ ID NO 31
<211> LENGTH: 17
<212> TYPE: PRT
<213> ORGANISM: Artificial Sequence
<220> FEATURE:
<223> OTHER INFORMATION: SYNTHETIC PEPTIDE

<400> SEQUENCE: 31

Tyr Ile Ser Arg Gly Gly Val Ser Thr Tyr Tyr Ser Asp Thr Val Lys
1               5                   10                  15

Gly

<210> SEQ ID NO 32
<211> LENGTH: 17
<212> TYPE: PRT
<213> ORGANISM: Artificial Sequence
<220> FEATURE:
<223> OTHER INFORMATION: SYNTHETIC PEPTIDE

```
<400> SEQUENCE: 32

Ala Ile Ser Arg Gly Gly Gly Tyr Ser Tyr Tyr Leu Asp Ser Val Lys
1               5                   10                  15

Gly

<210> SEQ ID NO 33
<211> LENGTH: 10
<212> TYPE: PRT
<213> ORGANISM: Artificial Sequence
<220> FEATURE:
<223> OTHER INFORMATION: SYNTHETIC PEPTIDE

<400> SEQUENCE: 33

Glu Lys Tyr Gly Lys Arg Gly Met Asp Tyr
1               5                   10

<210> SEQ ID NO 34
<211> LENGTH: 10
<212> TYPE: PRT
<213> ORGANISM: Artificial Sequence
<220> FEATURE:
<223> OTHER INFORMATION: SYNTHETIC PEPTIDE

<400> SEQUENCE: 34

Gln Lys Tyr Asn Lys Arg Ala Met Asp Tyr
1               5                   10

<210> SEQ ID NO 35
<211> LENGTH: 11
<212> TYPE: PRT
<213> ORGANISM: Artificial Sequence
<220> FEATURE:
<223> OTHER INFORMATION: SYNTHETIC PEPTIDE

<400> SEQUENCE: 35

Thr Ala Arg Ala Thr Trp Asp Trp Phe Ala Tyr
1               5                   10

<210> SEQ ID NO 36
<211> LENGTH: 52
<212> TYPE: PRT
<213> ORGANISM: Artificial Sequence
<220> FEATURE:
<223> OTHER INFORMATION: SYNTHETIC PEPTIDE

<400> SEQUENCE: 36

Lys Lys Lys Lys Lys Lys Lys Lys Lys Lys Lys Lys Lys Lys Lys
1               5                   10                  15

Lys Lys Lys Val Ala Tyr Ile Ser Arg Gly Gly Gly Ile Phe Tyr Tyr
                20                  25                  30

Gln Asp Ser Ile Lys Gly Arg Phe Thr Arg Glu Lys Tyr Gly Lys Arg
            35                  40                  45

Gly Met Asp Tyr
        50
```